(12) United States Patent  (10) Patent No.: US 8,805,484 B2
Syed et al.  (45) Date of Patent: Aug. 12, 2014

(54) SYSTEM, APPARATUS AND METHOD FOR DIAGNOSING SEIZURES

(75) Inventors: Tanvir U. Syed, Cleveland, OH (US); Farhad Kaffashi, Cleveland Heights, OH (US); Ken Loparo, Chesterland, OH (US); Hans O. Luders, Chagrin Falls, OH (US)

(73) Assignee: Case Western Reserve University, Cleveland, OH (US)

(*) Notice: Subject to any disclaimer, the term of this patent is extended or adjusted under 35 U.S.C. 154(b) by 0 days.

(21) Appl. No.: 13/564,441

(22) Filed: Aug. 1, 2012

(65) Prior Publication Data

US 2013/0041275 A1  Feb. 14, 2013

Related U.S. Application Data

(60) Provisional application No. 61/513,881, filed on Aug. 1, 2011.

(51) Int. Cl.
*A61B 5/0402* (2006.01)
*A61B 5/00* (2006.01)
*A61B 5/0452* (2006.01)
*A61B 5/0205* (2006.01)

(52) U.S. Cl.
CPC .............. *A61B 5/4094* (2013.01); *A61B 5/0452* (2013.01); *A61B 5/0205* (2013.01)
USPC ........................................................ 600/509

(58) Field of Classification Search
CPC .... A61B 5/4094; A61B 5/0452; A61B 5/0205
See application file for complete search history.

(56) References Cited

U.S. PATENT DOCUMENTS

| 2009/0069703 A1* | 3/2009 | Takla et al. ................... 600/509 |
| 2012/0271182 A1* | 10/2012 | Liao et al. .................... 600/508 |
| 2013/0116514 A1* | 5/2013 | Kroner et al. ................. 600/301 |

OTHER PUBLICATIONS

Toth, V., Hejjel, L., Fogarasi, A., Gyimesi, C., Orsi, G., Szucs, A., Kovacs, N., Komoly, S., Ebner, A. and Janszky, J. (2010), Periictal heart rate variability analysis suggests long-term postictal autonomic disturbance in epilepsy. European Journal of Neurology, 17: 780-787. doi: 10.1111/j.1468-1331.2009.02939.x.*

* cited by examiner

*Primary Examiner* — Michael Kahelin
(74) *Attorney, Agent, or Firm* — Tarolli, Sundheim, Covell & Tummino LLP

(57) ABSTRACT

Systems and methods can be used to help discriminate between epileptic and non-epileptic seizures based on a relationship between the postictal heart electrical activity and the preictal heart electrical activity. Also disclosed is an approach to determine an R-R interval by using a time-invariant complex wavelet transform.

37 Claims, 18 Drawing Sheets

US 8,805,484 B2

SYSTEM, APPARATUS AND METHOD FOR DIAGNOSING SEIZURES

CROSS REFERENCE TO RELATED APPLICATION

This disclosure claims the benefit of U.S. Provisional Patent Application No. 61/513,881, filed Aug. 1, 2011 and entitled SYSTEM, APPARATUS AND METHOD FOR DIAGNOSING SEIZURES, which is incorporated herein by reference in its entirety.

TECHNICAL FIELD

This disclosure relates to a system, device and method to facilitate diagnosing seizures.

BACKGROUND

Non-epileptic seizures are paroxysmal events that can mimic an epileptic seizure but do not involve abnormal, rhythmic discharges of cortical neurons. They can be caused by physiological or psychological conditions. The latter typically refers to psychogenic non-epileptic seizures (PNES), which are sometimes referred to as pseudoseizures. PNES is commonly mistaken as epileptic seizures resulting in accurate diagnosis. One tool that can be utilized to confirm a PNES diagnosis is video electroencephalogram (VEEG). VEEG is costly, time consuming and is not typically available in all locations and communities. Consequently, diagnostic delays often arise for PNES patients that can impose health and economic burdens on individuals in various population levels. In addition, misdiagnosed PNES patients can be unnecessary prescribed high doses of multiple anti-epileptic medications with potential for adverse affects. Additionally, patients with prolonged attacks may be needlessly intubated for initiation of anti-epileptic pharmacological sedation protocols.

Physiological non-epileptic seizures are disorders in which the brain malfunctions as a consequence of a physiologic abnormality outside the brain, such as low blood pressure, fainting (syncope), hypoglycemia, electrolyte imbalance, and other disorders. In addition to physiological and psychogenic non-epileptic seizures, non-epileptic seizures can also be a form of malingering, in which an individual feigns a seizure for explicit monetary or other fraudulent tangible gain. Examples of such gain include, but are not limited to, being released from prison, obtaining disability, and to make injury claims as part of a lawsuit (e.g., after a motor vehicle accident, injury at work).

SUMMARY

This disclosure relates to a system, apparatus and method that can be used to help diagnose a seizure.

In one example, a non-transitory machine readable medium having instructions can perform a method that includes detecting a preictal heart rate associated with a given seizure for a patient and detecting a postictal heart rate associated with the given seizure. A relationship can be quantified based on the postictal heart rate and the preictal heart rate and the given seizure can be classified as epileptic or non-epileptic based on the quantifying.

In another example, an apparatus to discriminate between epileptic and non-epileptic seizures can include non-transitory memory to store heart electrical measurement data for at least before and after a given seizure and a processor to access instructions stored in the memory. The instructions can include an interval selector to designate the heart electrical measurement data as preictal heart electrical data or postictal heart electrical data. The instructions can also include an index calculator programmed to determine an index based on the preictal heart electrical data and the postictal heart electrical data, the index quantifying a relationship between postictal heart electrical activity and preictal heart electrical activity. The instructions can also include va classifier to indicate whether the given seizure is epileptic or non-epileptic based on the index.

DETAILED DESCRIPTION

This disclosure relates to a system, apparatus and method that can be used to diagnose a seizure. In one example, the approach described herein provides for diagnosis of a non-epileptic seizure based on quantitative heart measurements, such as can be characterized by computing one or more heart rate indices. For example, the system, apparatus and method disclosed herein can be utilized to discriminate between epileptic seizure and physiologic non-epileptic seizures. In another example, this disclosure relates to an approach to improve heart rate measurements, such as can be employed for detecting the R-R interval of a cardiac (e.g., electrocardiogram-EKG) signal.

Figure 1:
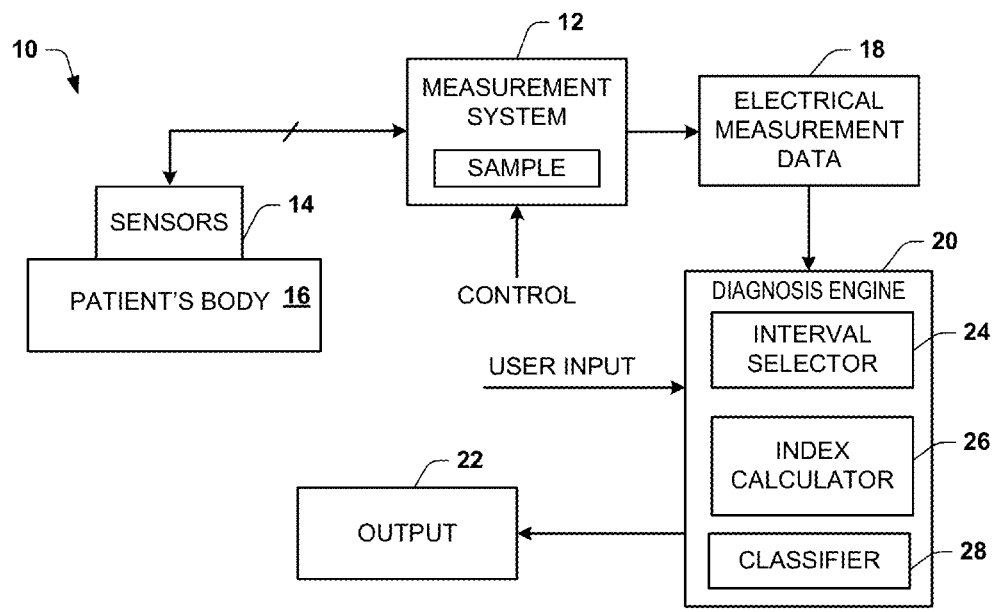
FIG. 1 depicts an example of a system to facilitate diagnosing a seizure.

FIG. 1 depicts an example of a system 10 that can be utilized to diagnose a seizure as either non-epileptic or epileptic. The system 10 can be implemented for diagnosing non-epileptic seizures in an inexpensive, time efficient and accessible alternative to VEEG. The system 10 can be implemented in different forms. In some examples, the system 10 (or at least a portion thereof) can be an ambulatory device that can be worn by a patient (e.g., similar to a Holter monitor). In other examples, the system 10 can be implemented in or be in communication with an existing EKG device to help diagnose a seizure as either non-epileptic or epileptic based on measured signals.

In the example of FIG. 1, the system 10 includes a measurement system 12 that receives inputs from a plurality of sensors 14 such as can include electrodes attached to an exposed surface of a patient's body 16. As an example, the sensors 14 can be implemented as precordial electrodes (e.g., three or more precordial leads) that are attached to sense electrical activity on the torso of the patient's body 16. In other examples, the sensors 14 can correspond to electrodes used in a twelve-lead EKG or other arrangements of electrodes that can be utilized to acquire EKG signals for the measurement system 12. Those skilled in the art will understand and appreciate various types and arrangements of sensor electrodes that can be utilized to acquire the cardiac electrical signals from the patient's body 16.

The measurement system 12 includes signal processing circuitry (e.g., filters, clock, sampling circuit, analog-to-digital converters and the like) configured to provide electrical measurement data, demonstrated at 18. The electrical measurement data 18 thus can correspond to digital representations of EKG signals acquired over time. The electrical measurement data 18 can be stored in memory or be provided as a continuous stream of digital data representing the measured EKG signals.

The measurement system 12 may receive a control input that can be utilized, for example, to identify timing for a patient event associated with the patient. For instance, the measurement system 12 can include a human-machine interface via which a user can designate beginning and end times for a seizure. Such user inputs can be employed to identify preictal and postictal periods for the electrical measurement data. The designation of preictal and postictal periods, for example, may be defined in response to pressing or otherwise activating a button or other user input interface to provide a control input signal to the measurement system 12. The temporal designation of measurement data 18 as preictal or postictal can be incorporated into the electrical measurement data by the measurements system 12. Since the patient experiencing the seizure will likely be unable to input the beginning and end of the seizure, another individual, such as a family member, nurse or other person can supply the input. In other examples, the system 10 can be programmed to automatically identify the period during which the seizure occurs in the electrical measurement data 18 and, in turn, designate one portion of the electrical measurement data 18 as the preictal data and another portion of the electrical measurement data as the postictal measurement data.

As a further example, the system 10 also includes a diagnosis engine 20 that is programmed to analyze the electrical measurement data 18 and diagnose a seizure for the patient. The diagnosis engine 20 can be implemented as computer-executable instructions that can be stored in a non-transitory computer-readable medium, which can be accessed and executed by a processor. The diagnosis engine 20 can be programmed to compute one or more heart rate indices from the electrical measurement data 18 and in turn classify the seizure as non-epileptic or epileptic based on an analysis heart rate index or indices. The diagnosis engine 20 thus can provide an output 22 identifying the seizure as being epileptic or non-epileptic. The output 22 can be stored in memory and/or provided to an output device, such as a display or other healthcare equipment. The system 10 can be utilized to diagnose different types of non-epileptic seizures, including physiological non-epileptic seizures, psychogenic non-epileptic seizures as well as malingering non-epileptic seizures.

The output 22 can be provided in one or more different forms depending upon the implementation of the system 10. For example, the output 22 can be provided on a display such as a computer screen, a display on a hand-held device, an audible output or the output can be provided as a printed record. Additionally or alternatively, the output 22 can include an electronic message that can be transmitted to one or more individuals via an appropriate messaging system (e.g., email, text message, instant messaging or the like) according to a predefined communications protocol. The output 22 can also be stored in a database, such as part of electronic patient record. The output 22 can be logical value (e.g., 0 or 1), specifying the diagnosis as epileptic or non-epileptic seizure. Alternatively, the output 22 can include other information, such as a percentage or a score indicating a likelihood of a seizure being epileptic or non-epileptic. Further information can be derived and provided in the output 22 to identify the type of non-epileptic seizure.

As mentioned above, portions of the system 10 can be implemented as computer executable instructions that can be employed to receive and process the electrical measurement data 18 to help diagnose a seizure. For instance, the electrical measurement data 18 may be transmitted (e.g., via a network, such as the Internet or an Intranet) from the measurement system 12 to a computer that is programmed with instructions corresponding to the diagnosis engine 20 to process the electrical measurement data according to the systems and methods disclosed herein to return a corresponding seizure diagnosis. The link for sending the EKG data can be wireless (e.g., Bluetooth, wireless LAN, cellular data) or be a physical connection (e.g., optical fiber or electrically conductive cable).

In the example of FIG. 1, the diagnosis engine 20 includes an interval selector 24 that can be programmed to select preictal and postictal data sets from the electrical measurement data 18. As mentioned above, the beginning and end of a seizure can be designated in response to a user input, which timing can be encoded (e.g., as a time index) in the electrical measurement data. The interval selector 24 can employ the timing information to determine a set of data corresponding to preictal heart data and another set of data corresponding to postictal heart data. For example, the preictal data set can include EKG data for a predetermined duration (e.g., about 2 to 5 minutes) prior to seizure onset. The interval selector 24 can also designate the postictal period as corresponding to a predetermined duration after the seizure has ended. The amount of postictal or preictal data can vary depending upon the circumstances relating to a given seizure.

The diagnosis engine 20 can also include an index calculator 26 programmed to calculate a heart rate index based on the preictal and postictal data sets. A heart rate index can quantify a characteristic of the heart electrical activity, such as heart rate, heart rate variability or a combination of heart electrical characteristics. Thus, as used herein, an index may include a set of one or more indices. By way of example, the index calculator 26 can compute a heart rate index to characterize one or more of the following: absolute heart rate change, relative heart rate change, provide an indication of short-term heart rate variability, long-term heart rate variability as well a characterize low frequency and high frequency signal content in the heart rate as well as combinations thereof. The heart rate index may also reflect other preictal and postictal patient physiological conditions that can be monitored (e.g., respiration rate, pulse oximetry, etc.) by the measurement system 12. The index calculator 26 can employ descriptive statistics, inferential statistics, signal analysis or other analytics to compute the heart rate index based on the postictal and preictal heart electrical activity.

The diagnosis engine 20 can also include a classifier 28 that is programmed to classify a given seizure episode as epileptic or non-epileptic based upon index provided by the index calculator 26. The classifier 28, for example, can employ the heart rate index to diagnose a given seizure as epileptic or non-epileptic. Based on the classification determined by the classifier 28, the diagnosis engine 20 provides a corresponding output 22.

Figure 2:
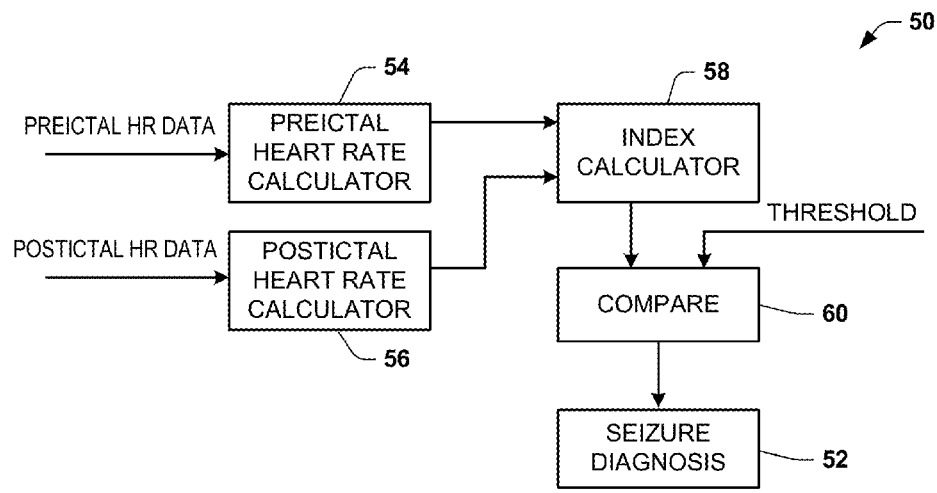
FIG. 2 depicts an example of an apparatus that can be implemented to help diagnose a seizure.
Figure 3:
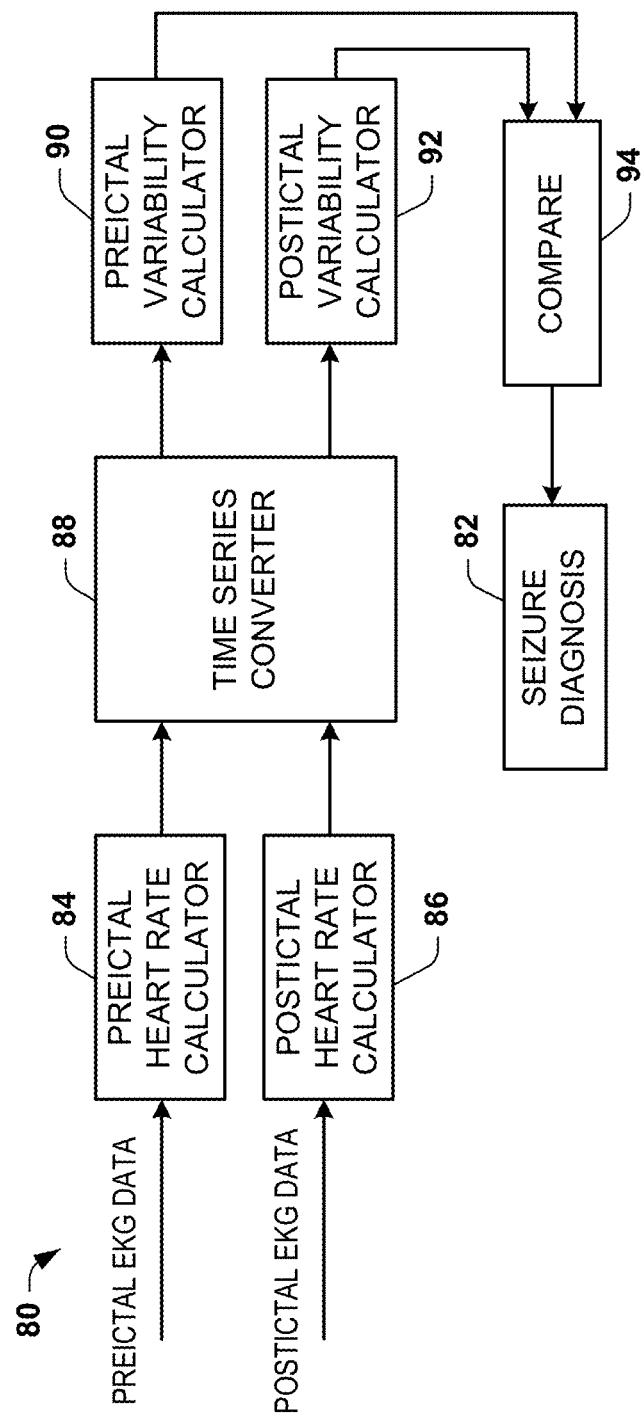
FIG. 3 depicts another example of an apparatus that can be implemented to help diagnose a seizure.
Figure 4:
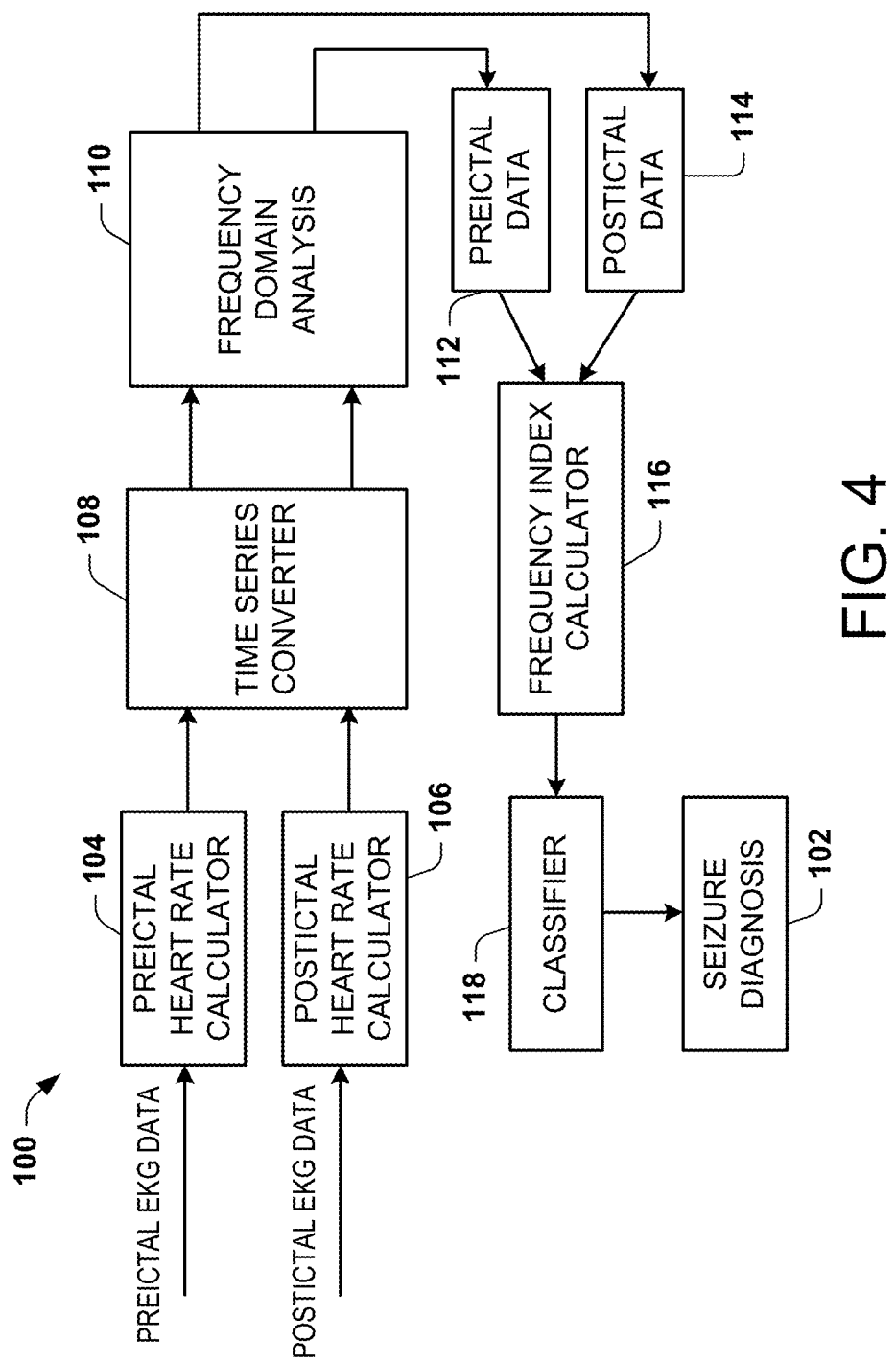
FIG. 4 depicts yet another example of an apparatus that can be implemented to help diagnose a seizure.

FIGS. 2, 3 and 4 provide examples of apparatuses that can be employed to determine different heart rate indices that may be utilized for classifying a seizure as epileptic or non-epileptic. The respective apparatuses in FIGS. 2, 3 and 4 can be implemented as computer executable instructions that are stored in memory, which can be accessed and executed by a processor. For each of the examples of FIGS. 2, 3 and 4, the different embodiments receive preictal heart rate data and postictal heart rate data, such as can be extracted from electrical measurement data provided by a measurement system (e.g., the measurement system 12 of FIG. 1). For instance, the measurement system can correspond to any type of EKG device, such as may correspond to an existing EKG device or a device specially adapted for providing EKG data in the context of the systems and methods disclosed herein.

FIG. 2 depicts an example of an apparatus 50 that can be implemented for helping provide a seizure diagnosis 52. In the example of FIG. 2, the apparatus 50 can provide the seizure diagnosis 52 based upon a heart rate index that characterizes a relative heart rate change. The diagnosis apparatus 50 includes a preictal heart rate calculator 54 and a postictal heart rate calculator 56.

Each of the heart rate calculators 54 and 56 can be programmed to compute preictal and postictal heart rate, respectively. The calculators 54 and 56 can compute the preictal heart rate from R-R intervals computed over a preictal period and the postictal heart rate over a postictal period. Those skilled in the art will understand and appreciate various R-R detection algorithms that may be implemented. One example approach that can be utilized to accurately identify the R-wave and thus can be utilized for determining the R-R interval is disclosed herein in relation to FIG. 18. Other means for computing heart rate could alternatively be utilized by the respective calculators 54 and 56.

A heart rate index calculator 58 can compute a heart rate index to characterize a relative heart rate change preictally and/or postictally. The index calculator 56 can compute the heart rate index as a standardized statistical score, such as a Z-score. For example, the Z-score can represent an absolute heart rate change ($HR_{postictal} - HR_{preictal}$) divided by the standard deviation of a preictal heart rate. The relative heart rate change defined by the index thus takes into account a level heart rate fluctuation that is normal or baseline for a given patient. For example, a preictal-to-postictal heart rate change of 15 bpm may not indicate a significant change in a patient whose baseline heart rate fluctuates by 10 bpm, but may indicate a drastic change in an individual whose baseline heart rate fluctuates by 5 bpm.

The index calculator 56 provides the computed heart rate index to a compare block 60. The compare block 60 can compare the heart rate index relative to a threshold. The threshold can be selected, for example, as a function of the standard deviation of the preictal heart rate (e.g., corresponding to two standard deviations). Thus, if the heart rate index exceeds the threshold, the seizure can be classified as epileptic, whereas if the heart rate index is below the threshold, the compare function can identify the seizure as non-epileptic. The threshold can be fixed or it can be variable (e.g., programmable) such as may vary depending on a condition of the patient.

FIG. 3 depicts an example of a diagnosis apparatus 80 that can help classify and provide a seizure diagnosis 82 based upon an index characterizing at least one of short-term and long-term heart variability. In the example of FIG. 3, the apparatus 80 includes a preictal heart rate calculator 84 and a postictal heart rate calculator 86. Each of the respective calculators 84 and 86 operates to compute preictal and postictal heart rate for a selected preictal duration and selected postictal duration. The heart rate calculator 84, for example, can compute the preictal heart rate corresponding to R-R intervals in the preictal data set and the heart rate calculator 86, for example, can compute the postictal heart rate corresponding to R-R intervals in the postictal data set. Those skilled in the art will understand and appreciate various heart rate detection algorithms that may be implemented based on this disclosure.

In the example of FIG. 3, a time series converter 88 converts each of the computed preictal and postictal heart rates to a time series representation of consecutive R-R intervals. The time series converter 88 may be implemented as a function within the calculators 84 and 86, for example. The time series converter 88 provides the time series representations of consecutive R-R intervals to variability calculators 90 and 92, respectively.

Each of the variability calculators 90 and 92 can be programmed to compute short-term variability, long-term variability, or information characterizing a relationship between short-term and long-term variability such as a ratio therebetween. As one example, each of the variability calculators 90 and 92 can be programmed to construct a Poincare' plot in an x-y plane in which each point represents a pair of R-R intervals. For example, each R-R interval pair may correspond to each adjacent or sequential R-R interval or can correspond to other pairs such as every third, every fourth, or other types of mathematical relationships between respective R-R intervals. The resulting plot of R-R intervals can define an elliptical curve that statistically fits the variability data thereby having a major axis and a minor axis. The length of the minor axis can be derived to represent short-term variability for the R-R intervals and the length of the major axis of the plotted ellipse can correspond to long-term variability. A short-term variability to long-term variability (ST/LT) ratio can represent a numerical quotient of short-term and long-term variability for a given plot. While the foregoing example, describes the calculators 90 and 92 as constructing a plot (e.g., a Poincare' plot), it is understood that the corresponding calculations can be implemented in the absence of actually plotting the data in the form of a graph.

As just described, the variability calculator 90 can be programmed to estimate short-term variability, long-term variability and a ratio of short-term to long-term variability for the preictal period. Similarly, the variability calculator 92 can compute short-term variability, long-term variability and a ratio of short-term and long-term variability for the postictal period. The estimated values determined by the calculators 90 and 92 can correspond to respective preictal and postictal heart rate indices. A compare function 94 can be provided to compare relationships between the respective preictal and postictal indices to in turn classify and provide the seizure diagnosis 82, such as by discriminating between non-epileptic and epileptic seizures based on the comparison.

FIG. 4 depicts another example of a seizure diagnosis apparatus 100 that is operative to generate the seizure diagnosis 102 based on heart rate indices characterizing heart rate frequency for preictal and postictal periods. Similar to the example of FIG. 3, the apparatus 100 includes preictal and postictal heart rate calculators 102 and 104 programmed to compute beat to beat heart rate from preictal and postictal EKG data, such as is generated by an EKG device or specialized EKG measurement system. A time series converter 108 is programmed to convert the computed heart rate information into a time series representation of consecutive R-R intervals for each of the preictal and postictal periods.

In the example of FIG. 4, frequency domain analysis block 110 is programmed to analyze the time series representation of the preictal and postictal time series representation, such as by computing a discrete Fourier transform on the time series representation of the R-R intervals. For example, the frequency domain analysis 110 can employ an appropriately modified fast Fourier transform (FFT) algorithm to convert the non-uniformly sampled time domain data into corresponding data in the frequency domain. The frequency domain analysis block 110 thus produces preictal frequency data 112 and postictal frequency data 114 characterizing the frequency content within each of the respective time series representations.

As an example, the frequency domain analysis block 110 can generate a power spectral density function that characterizes the frequency content provided by each of the preictal and postictal time series representations of R-R intervals. Within the spectrum of the power spectrum density function, high frequency and low frequency peaks can exist in each of the preictal frequency data 112 and postictal frequency data 114 sets.

A frequency index calculator 116 can be programmed to compute one or more frequency indices based on the preictal frequency data 112 and postictal data 114. For example, the frequency index calculator 116 can extract indices corresponding to a low frequency peak and a high frequency peak in the power spectral density functions, as characterized by the preictal and postictal frequency data 112 and 114. Additionally or alternatively, the frequency index calculator 116 can compute a ratio between the high frequency and low frequency indices to provide another aggregate index, such as may reflect non-linear dynamics associated with heart rate variability. A classifier 118 can in turn employ the index generated by the frequency index calculator to provide the seizure diagnosis 102, discriminating between a non-epileptic seizure and an epileptic seizure based on the index.

From the foregoing examples of FIGS. 1-4, it is to be understood and appreciated that a classifier can be implemented to classify a seizure as epileptic or non-epileptic based on one or more computed indices. In each of these examples, weighting can be utilized and selectively applied to one or more indices. For example, such weighting of indices can vary according to a type of seizure as well as the age or other physiological conditions of the patient (e.g., seizure duration, age, co-morbidities or the like).

As an additional or alternative example, various thresholds may be adapted for a given index or a combination of indices to facilitate accurate diagnosis of seizure conditions. For example, the classifier can employ multiple heart rate indices (two or more indices disclosed herein) simultaneously to enhance the predictive power of the diagnosis. Weighting of the respective indices can be determined via various analysis and descriptive statistics such as including discriminated analysis, multiple logistic regression, artificial neuron networks, data fusion or other forms of artificial intelligence, such as based on analysis of ROC (receiver operating characteristic) curves or other evaluation techniques.

FIGS. 5-16 demonstrate examples of plots of data acquired from patients that can be utilized to help diagnosis seizures as epileptic or non-epileptic. The underlying data and associated plots can be analyzed as disclosed herein to determine thresholds for respective indices to facilitate accurate seizure diagnoses.

Figure 5:
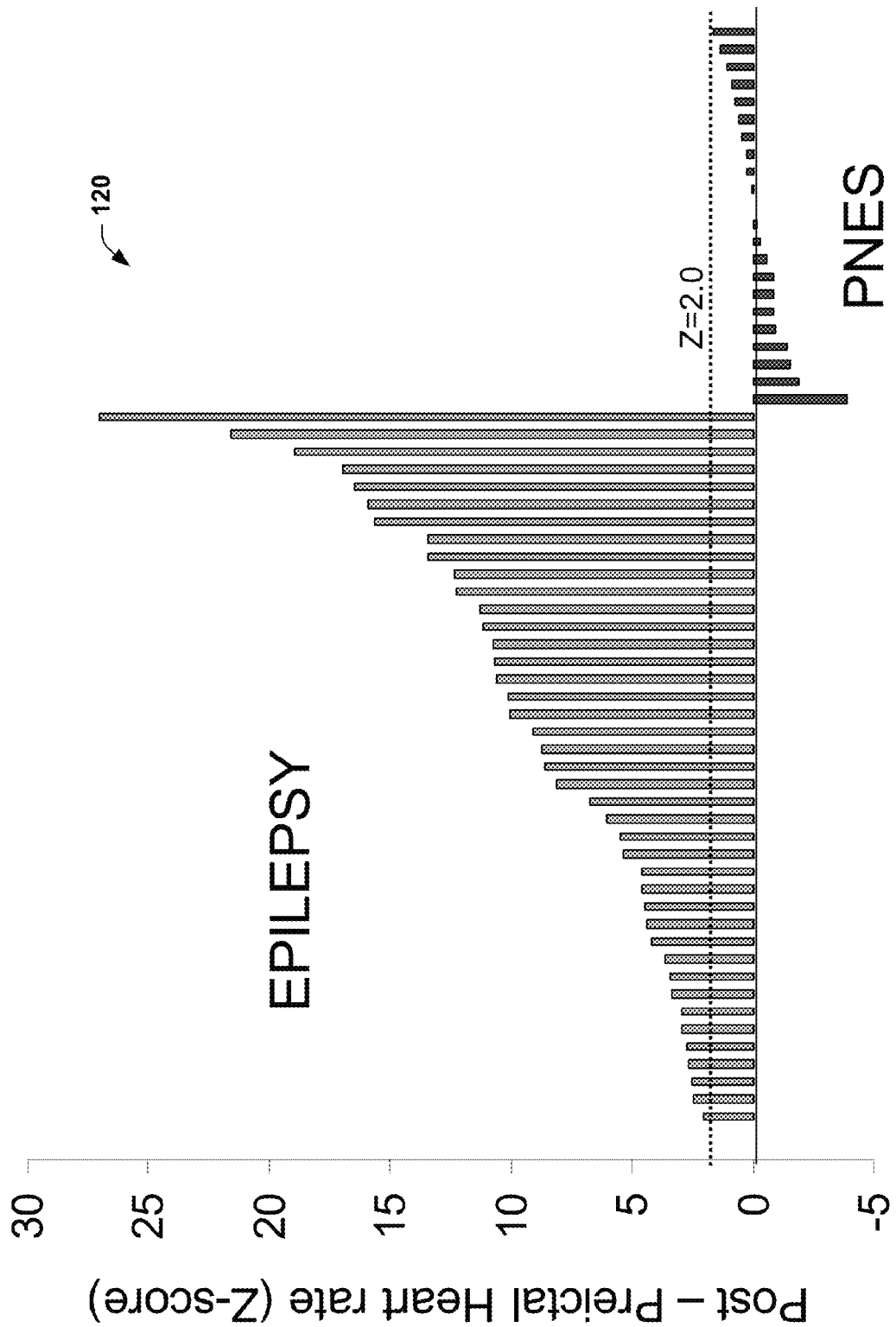
FIG. 5 is a bar graph depicting heart rate change for a patient population for demonstrating an example approach for diagnosing a seizure.

FIG. 5 depicts an example of a bar graph 120 of heart rate indices for patients demonstrating a Z-score for different patients. The example of FIG. 5 demonstrates the relative heart rate change in terms of a Z-score calculated based upon the preictal heart rate and postictal heart rate such as disclosed herein with respect to the example diagnosis apparatus 50 of FIG. 2. It was determined that, for motor-type seizures and with a threshold of approximately Z=2, patients having a Z-score greater than the threshold had epileptic seizures, whereas patients having a Z-score less than the threshold had non-epileptic seizures (e.g., PNES).

Figure 6:
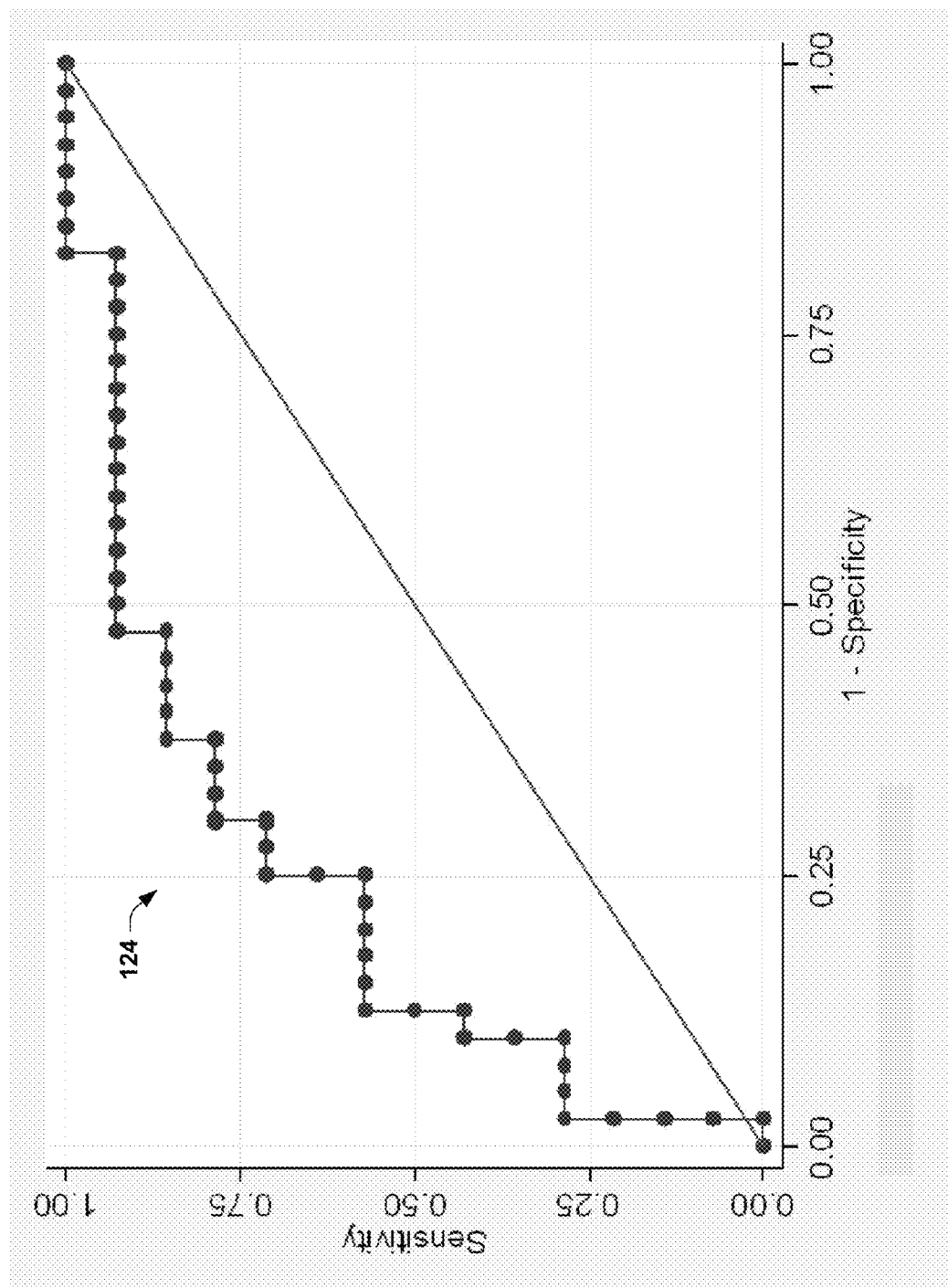
FIG. 6 is a graphical plot of sensitivity depicting heart rate change for a patient population for demonstrating an example of analysis that can be utilized in diagnosing a seizure.

FIG. 6 depicts an example of a ROC curve 124 for an index corresponding to relative heart rate change in terms of a Z-score for non-motor type seizures. The example of FIG. 6 demonstrates the area under the ROC curve 124 to be equal to about 0.78.

Figure 7:
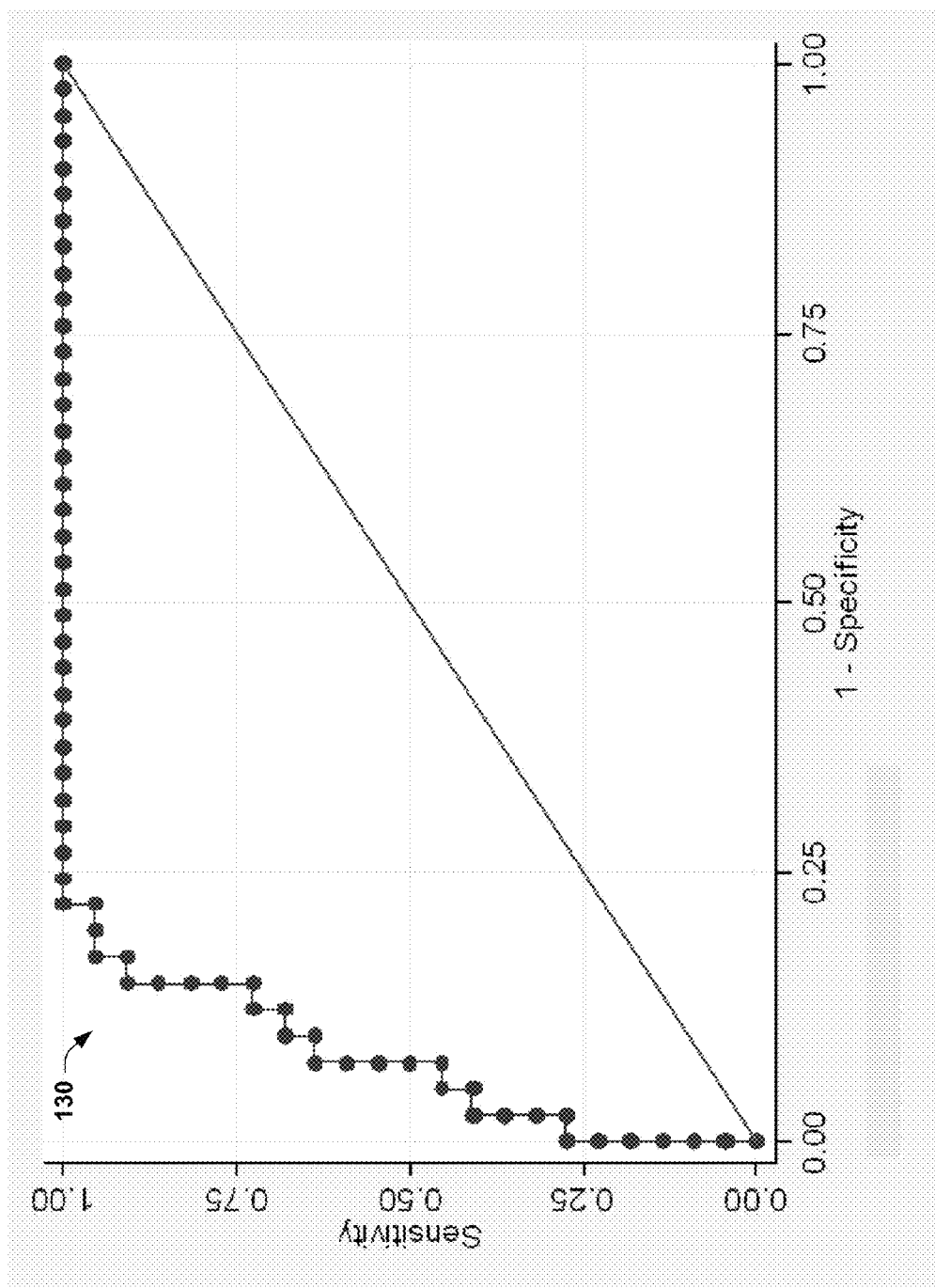
FIG. 7 is a graphical plot of sensitivity depicting heart rate change for a patient population for demonstrating an example of analysis that can be utilized in diagnosing a seizure.

FIG. 7 depicts an example of a ROC curve 130 for an index corresponding to a ratio of postictal to preictal standard deviations for motor type seizures. The example of FIG. 7 demonstrates the area under the ROC curve 130 to be equal to about 0.93.

Figure 8:
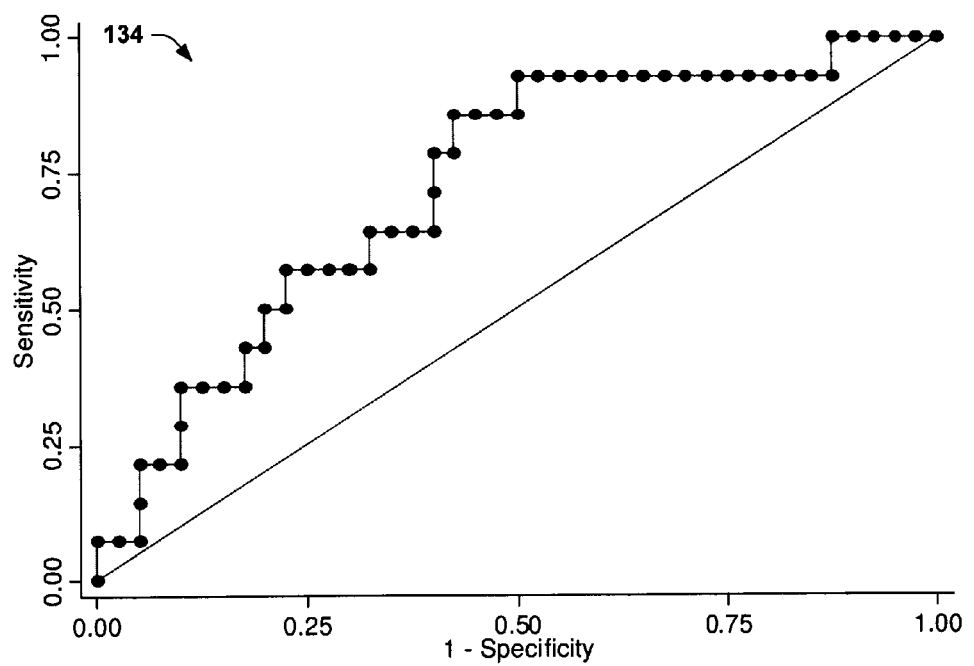
FIG. 8 is a graphical plot of sensitivity depicting heart rate change for a patient population for demonstrating an example of analysis that can be utilized in diagnosing a seizure.

FIG. 8 is similar to FIG. 7 demonstrating a ROC curve 134 for an index corresponding to the ratio of postictal to preictal standard deviations although for non-motor type seizures. The example of FIG. 8 demonstrates an area under the ROC curve 134 equal to about 0.73.

Figure 9:
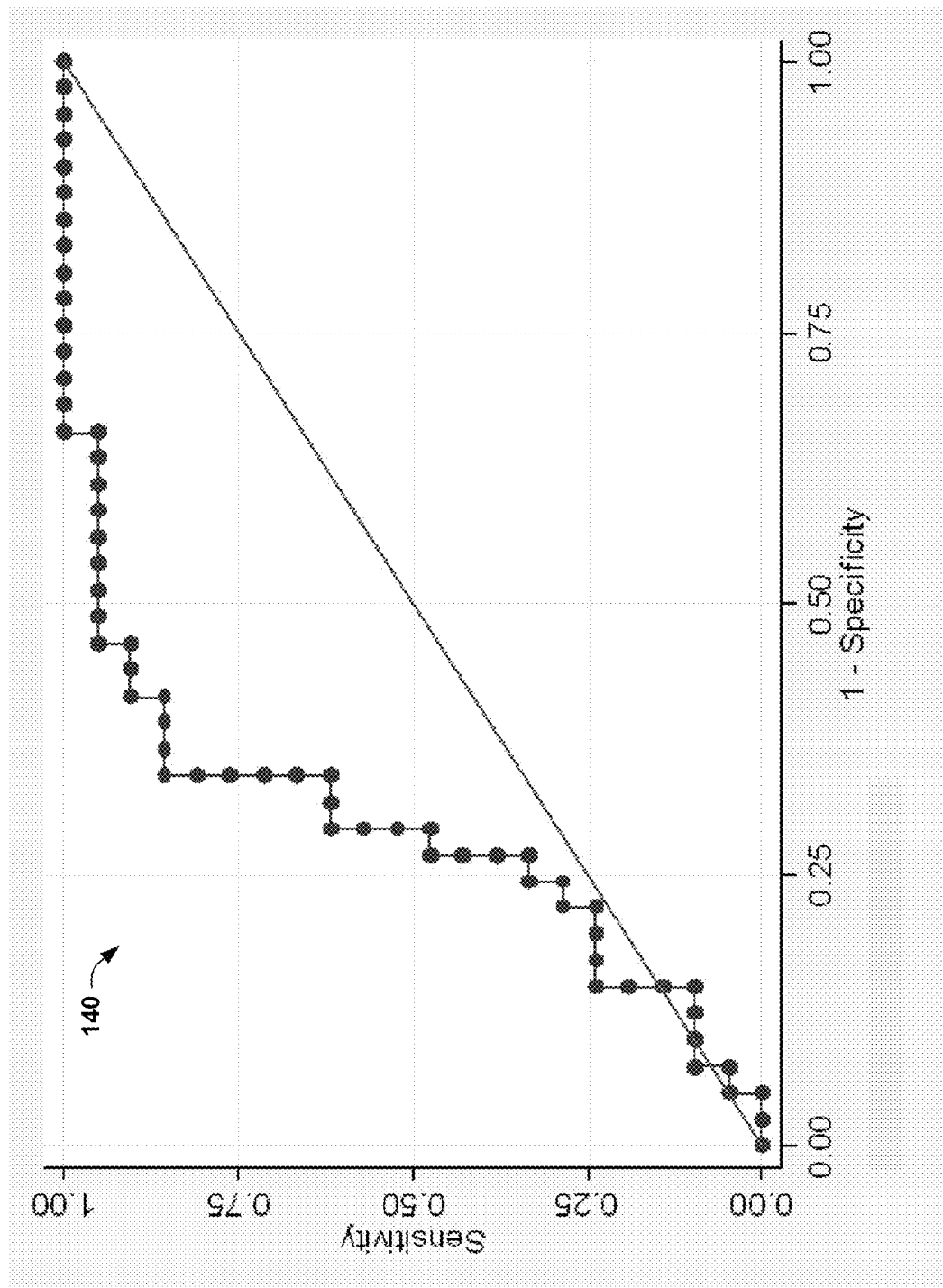
FIG. 9 is a graphical plot of sensitivity depicting heart rate change for a patient population for demonstrating an example of analysis that can be utilized in diagnosing a seizure.

FIG. 9 depicts an example of a ROC curve 140 for an index corresponding to a ratio of postictal to preictal short-term variability for motor type seizures. The postictal the short-term axis for example can correspond to an index that is generated by the example apparatus 80 of FIG. 3. The data in the example of FIG. 9 demonstrates an area under the ROC curve 140 of about 0.72.

Figure 10:
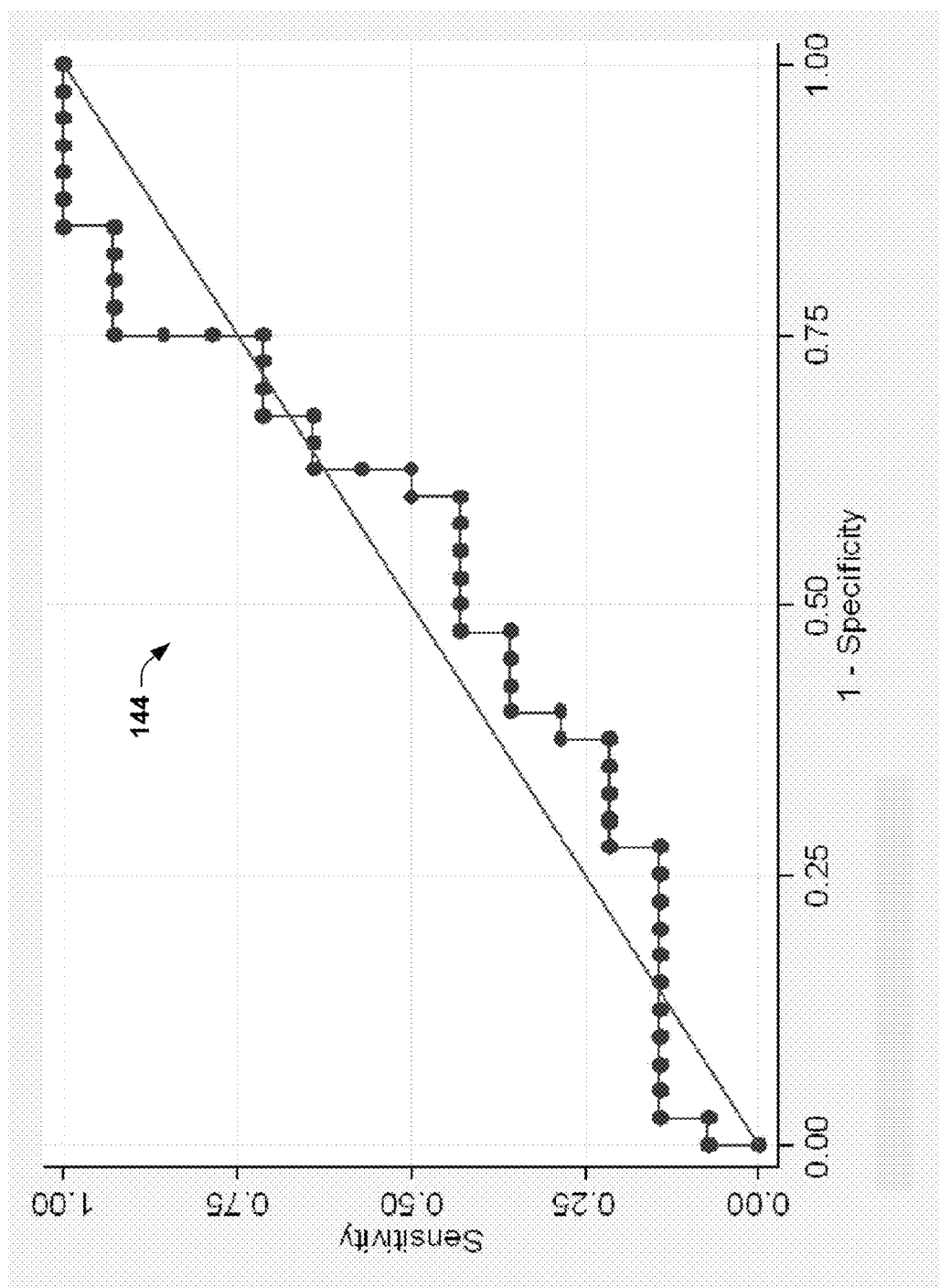
FIG. 10 is a graphical plot of sensitivity depicting heart rate change for a patient population for demonstrating an example of analysis that can be utilized in diagnosing a seizure.

FIG. 10 depicts an example of a ROC curve 144 for an index corresponding to a ratio of postictal to preictal short-term variability for non-motor type seizures. The example of FIG. 10 demonstrates an area under the ROC curve 144 of about 0.49.

Figure 11:
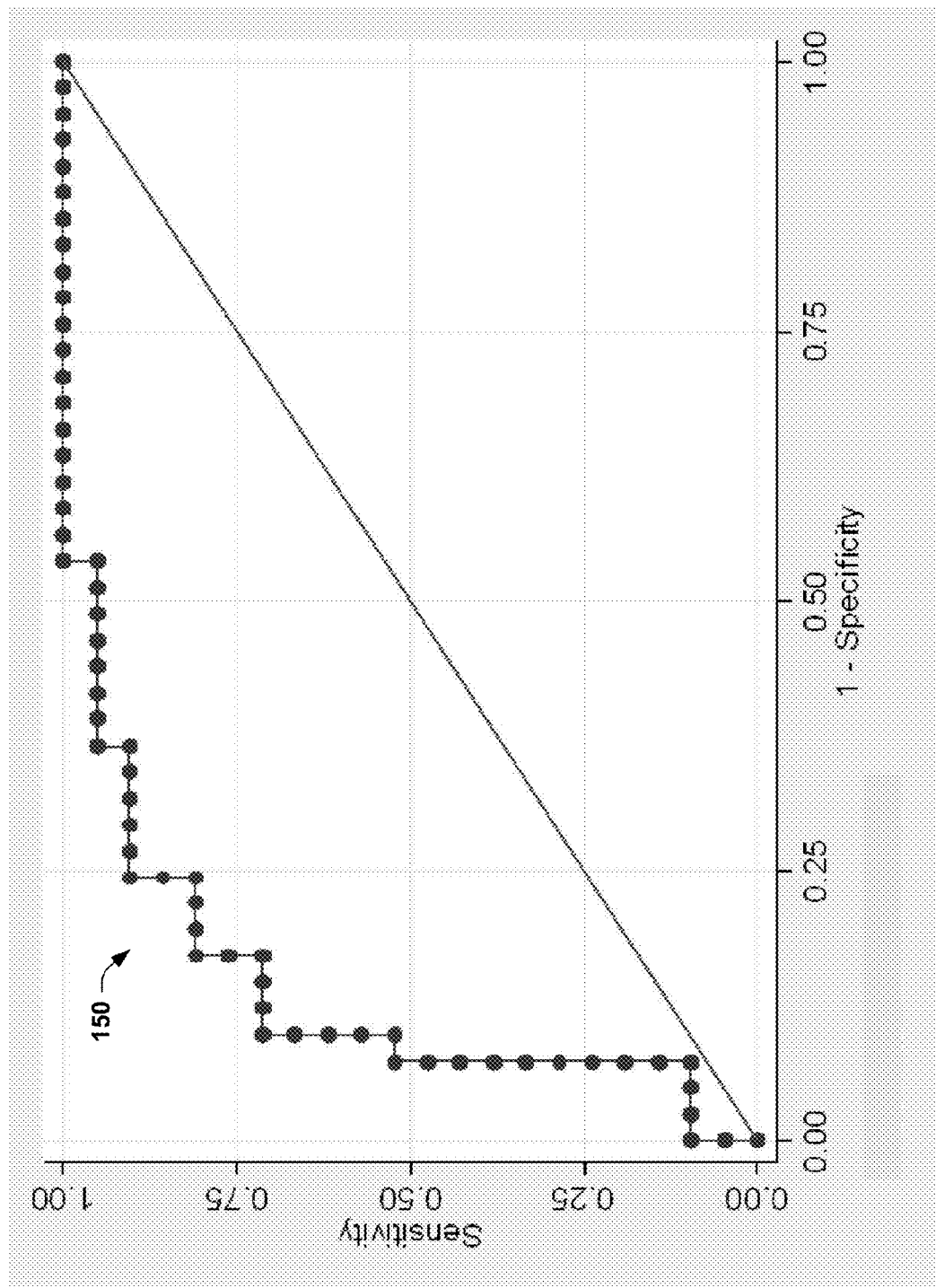
FIG. 11 is a graphical plot of sensitivity depicting heart rate change for a patient population for demonstrating an example of analysis that can be utilized in diagnosing a seizure.

FIG. 11 depicts an example of a ROC curve 150 for an index corresponding to a ratio of postictal to preictal long-term heart rate variability for a motor type seizure such as can be generated via the apparatus 80 of FIG. 3. In the example of FIG. 11, the area under the ROC curve is about 0.87.

Figure 12:
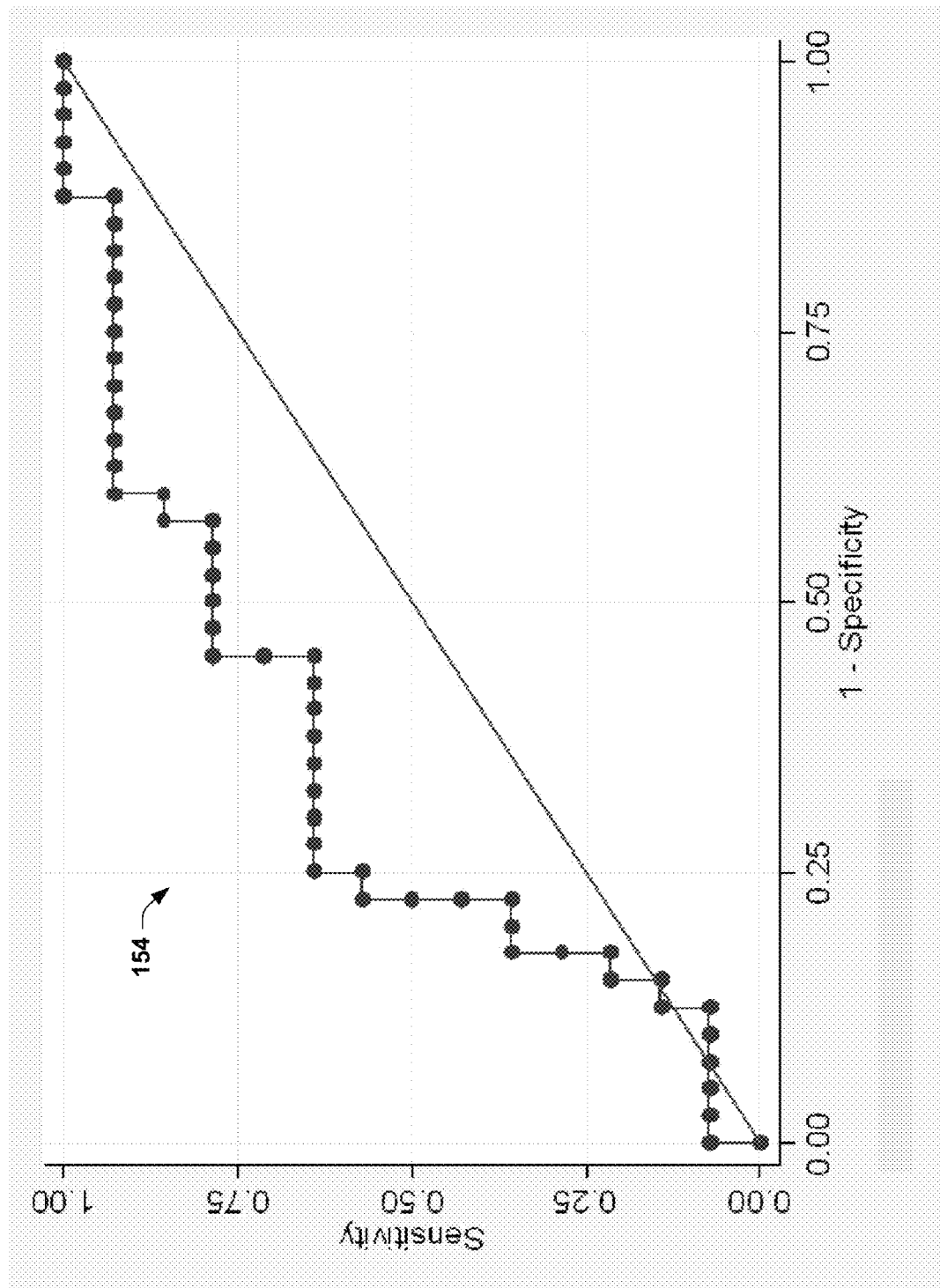
FIG. 12 is a graphical plot of sensitivity depicting heart rate change for a patient population for demonstrating an example of analysis that can be utilized in diagnosing a seizure.

FIG. 12 depicts an example of a ROC curve 154 for an index corresponding to a ratio of postictal to preictal long-term heart rate variability for non-motor types seizures. In the example of FIG. 12, the area under the ROC curve is about 0.68.

Figure 13:
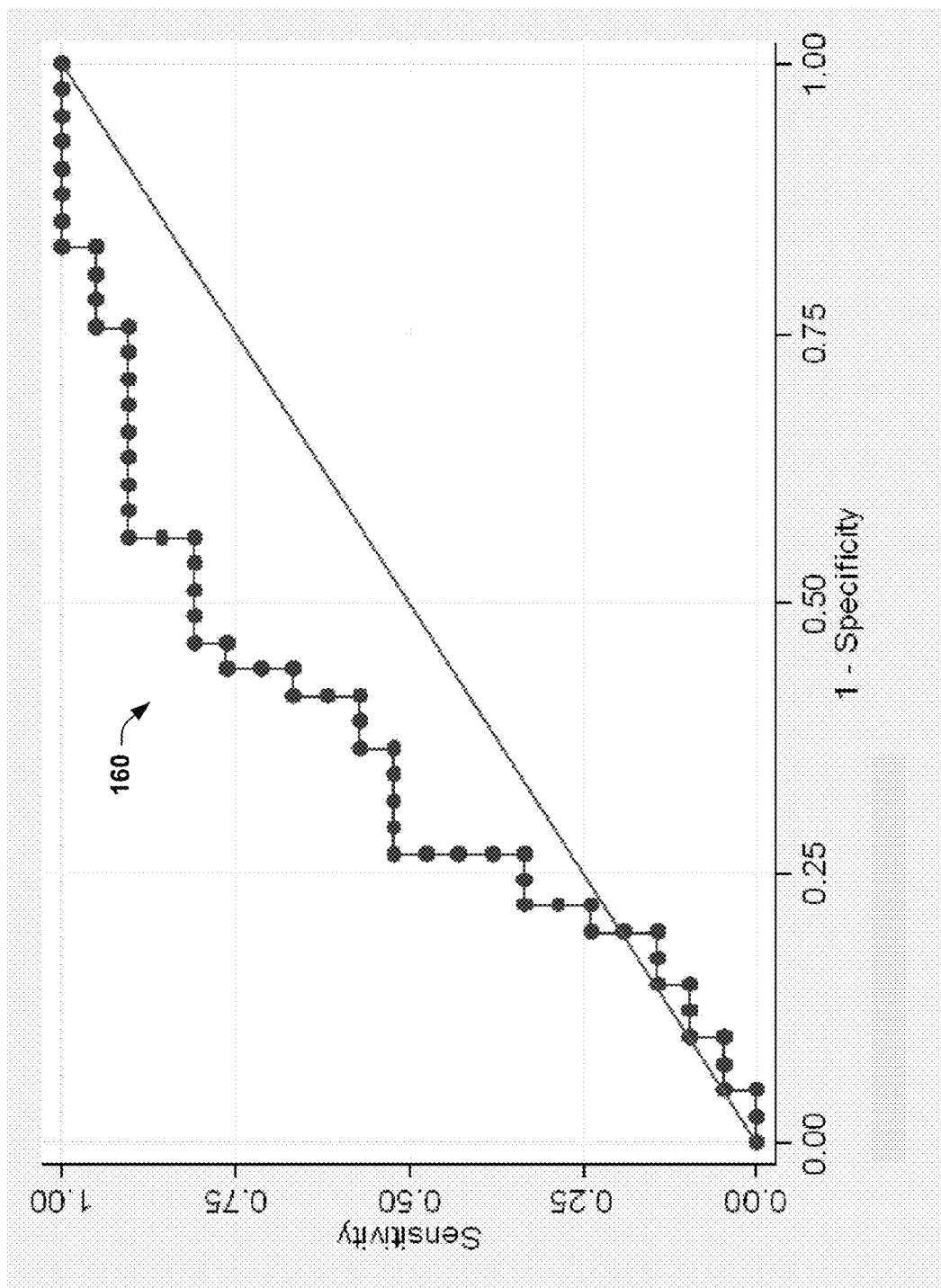
FIG. 13 is a graphical plot of sensitivity depicting heart rate change for a patient population for demonstrating an example of analysis that can be utilized in diagnosing a seizure.

FIG. 13 depicts an example of an ROC curve 160 for an index corresponding to a ratio of postictal to preictal short-term to long-term heart rate variability (ST/LT) for motor type seizures. In the example of FIG. 13 the area under the ROC curve 160 was determined to be about 0.65.

Figure 14:
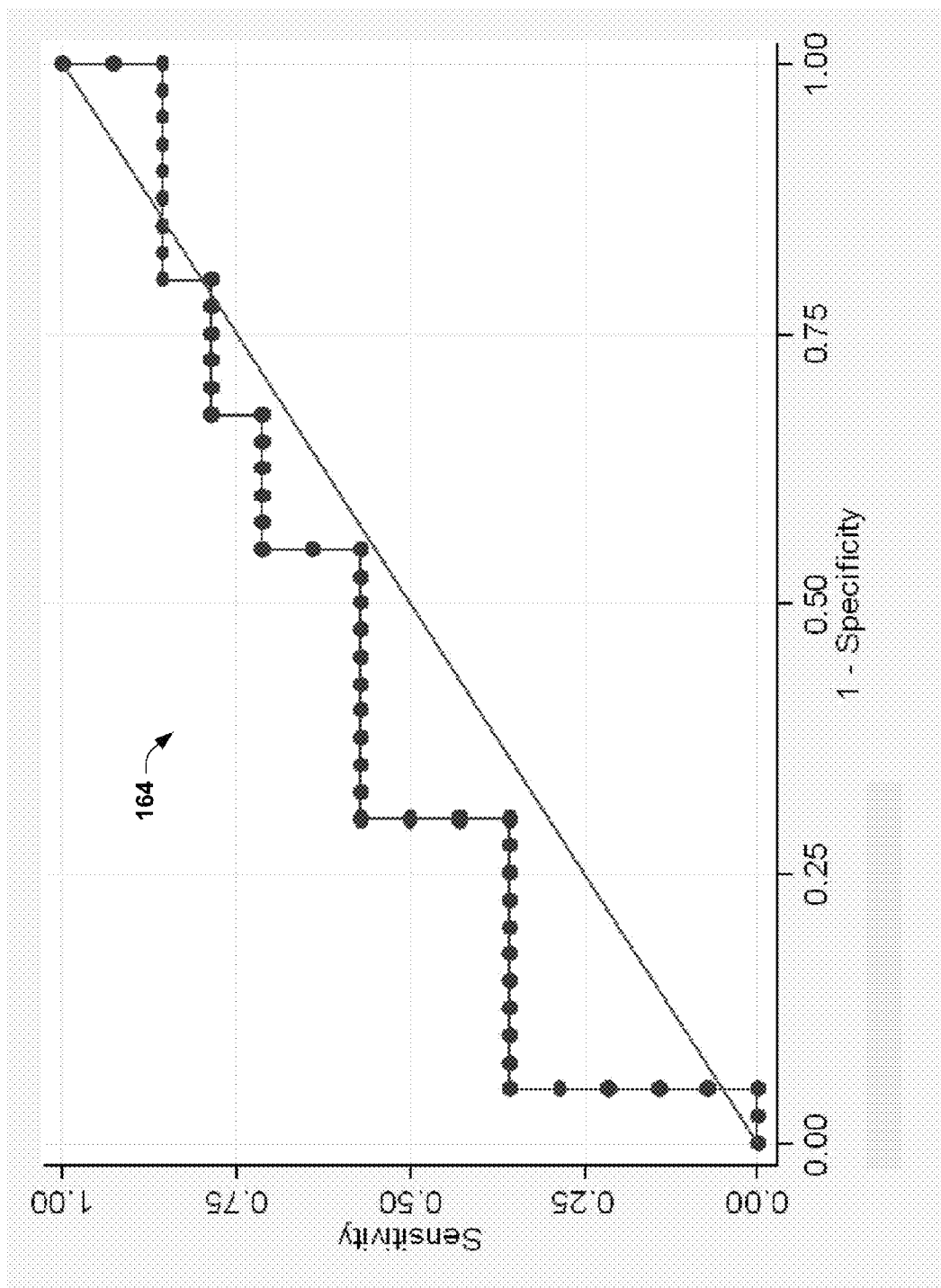
FIG. 14 is a graphical plot of sensitivity depicting heart rate change for a patient population for demonstrating an example of analysis that can be utilized in diagnosing a seizure.

FIG. 14 depicts an example of an ROC curve 164 for an index corresponding to a ratio of postictal to preictal short-term to long-term heart rate variability (ST/LT) for non-motor type seizures. In the example of FIG. 14, the area under the ROC curve 164 is about 0.59.

Figure 15:
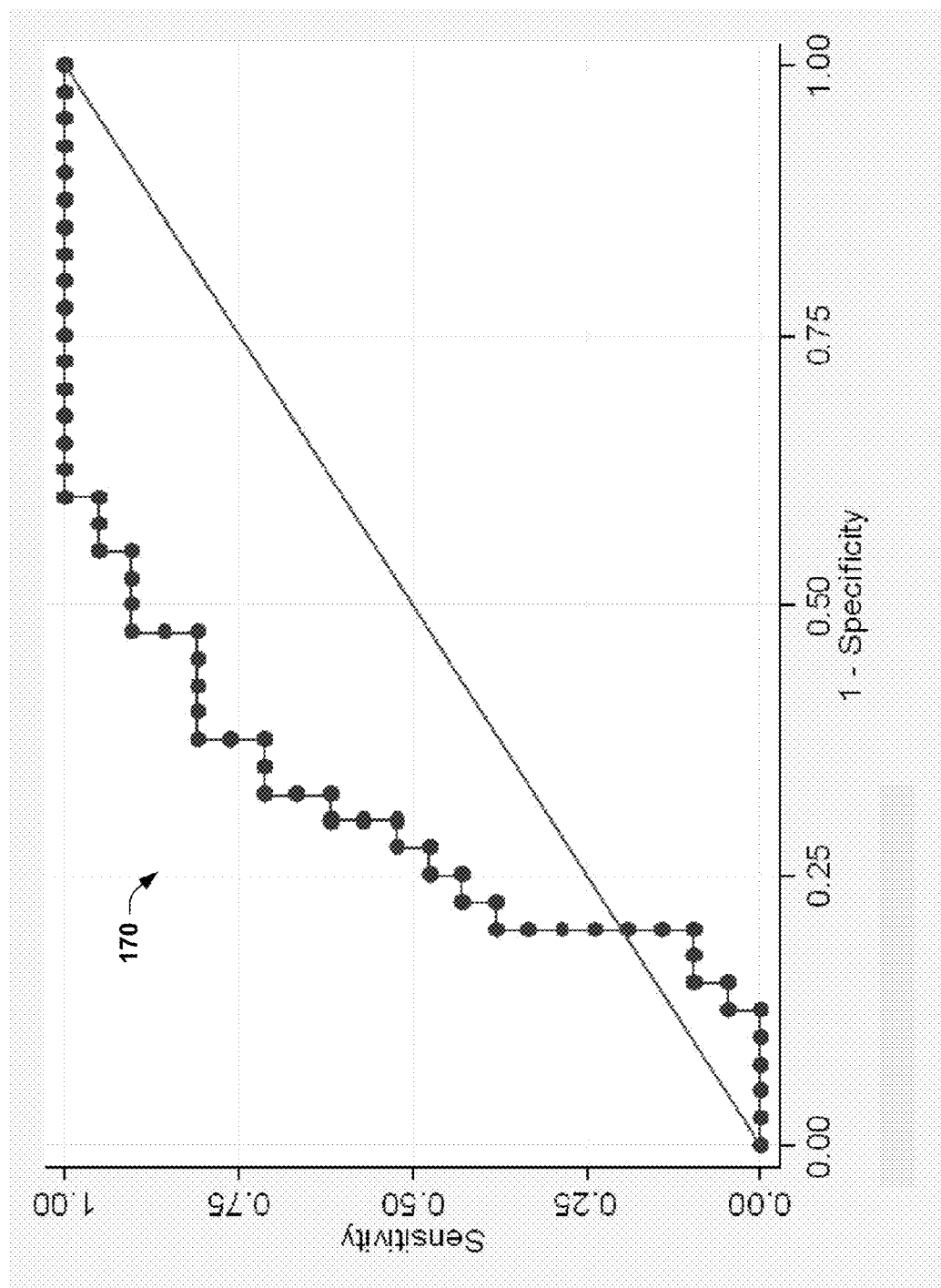
FIG. 15 is a graphical plot of sensitivity depicting heart rate change for a patient population for demonstrating an example of analysis that can be utilized in diagnosing a seizure.

FIG. 15 demonstrates an example of an ROC curve 170 for an index corresponding to a relative change in heart rate variability (e.g., a Z-score) postictally for minute 1 to minute 3 for motor type seizures. In the example of FIG. 15, the area under the ROC curve 170 is about 0.70.

Figure 16:
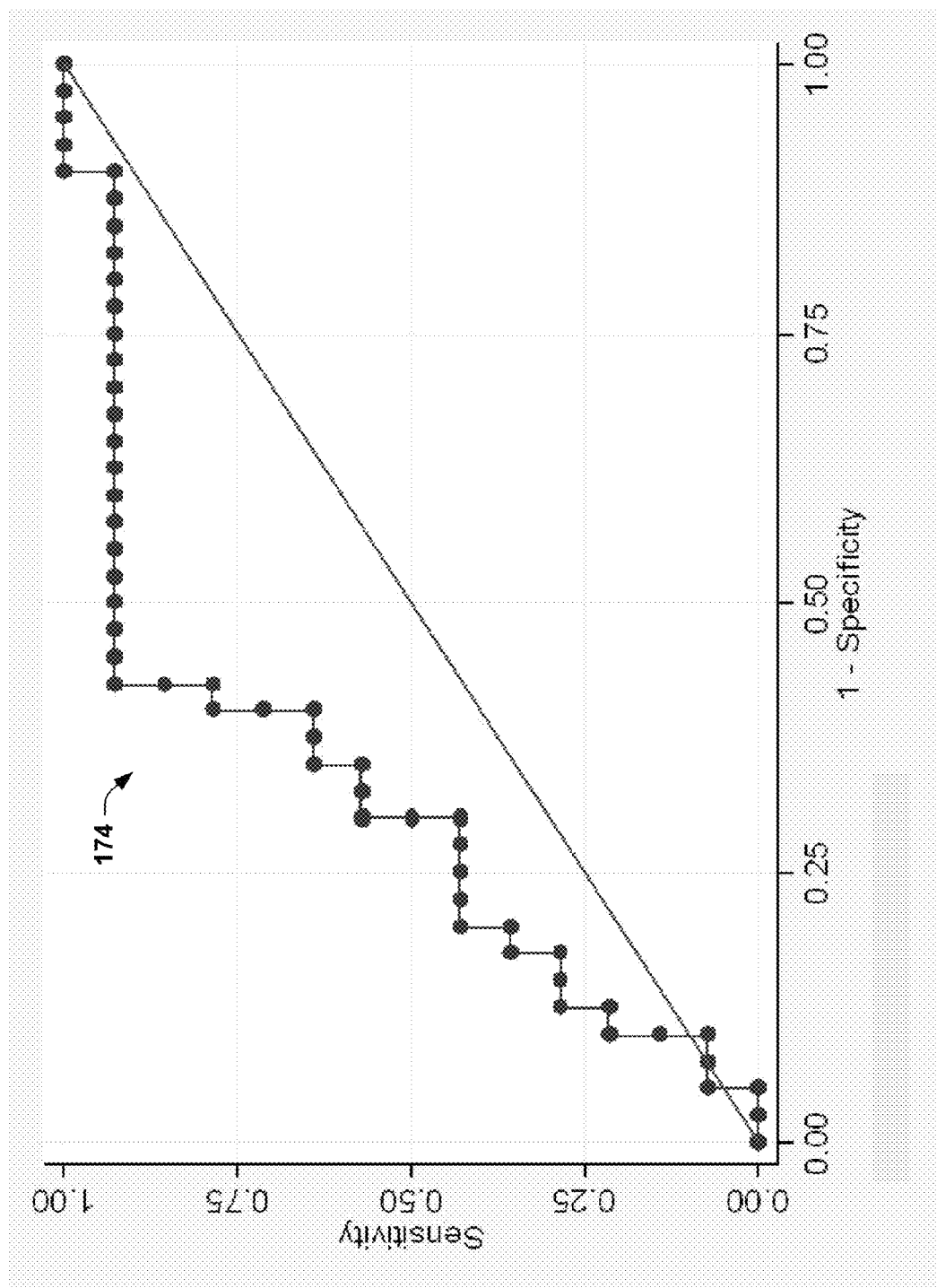
FIG. 16 is a graphical plot of sensitivity depicting heart rate change for a patient population for demonstrating an example of analysis that can be utilized in diagnosing a seizure.

FIG. 16 depicts an example of an ROC curve 174 for an index corresponding to a change (Z-score) postictally from minute 1 to minute 3 for non-motor type seizures. The example of FIG. 16 demonstrates an area under the ROC curve 174 of about 0.70.

Figure 17:
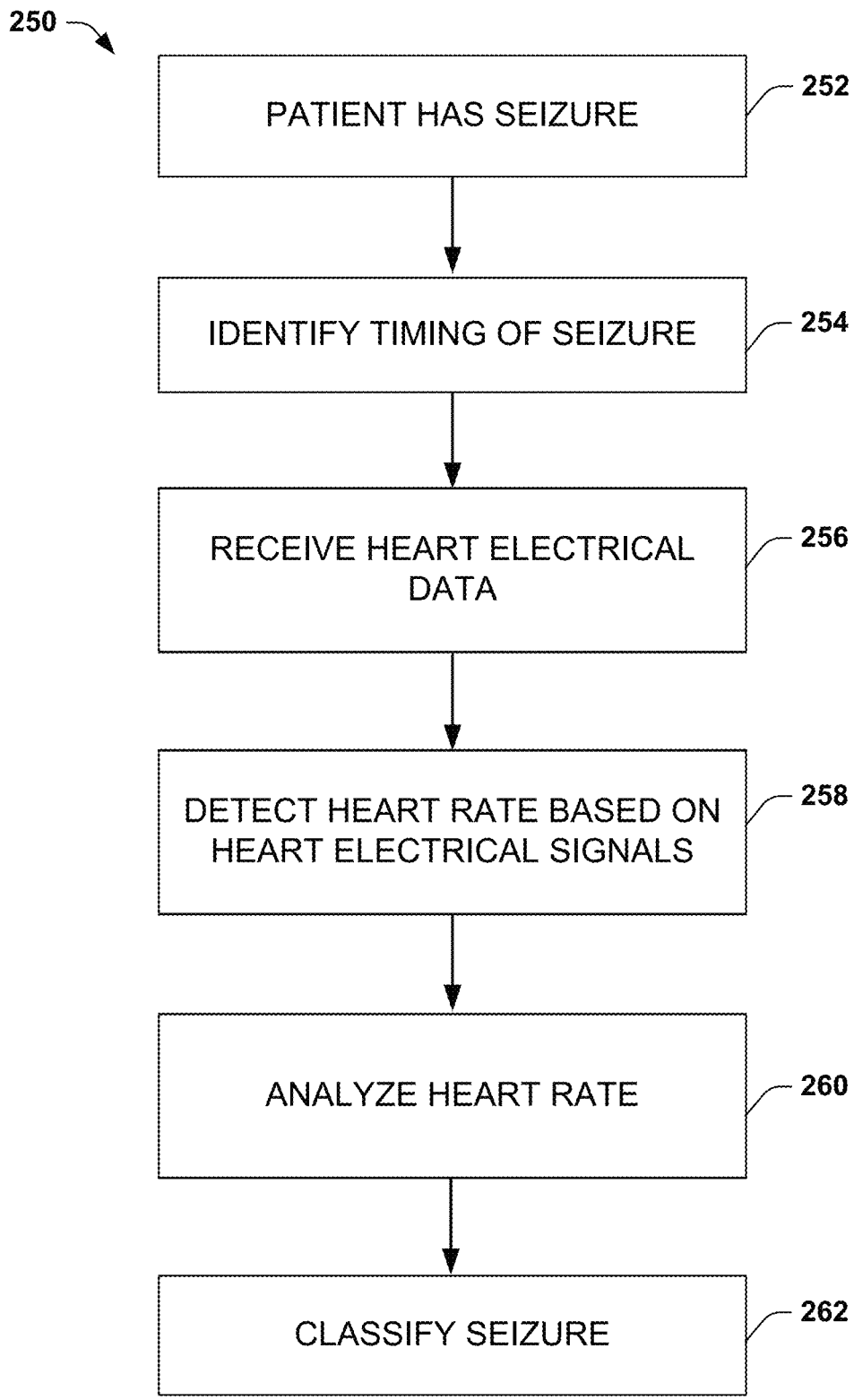
FIG. 17 is a flow diagram illustrating an example of a method that can be implemented to diagnose a seizure.
Figure 18:
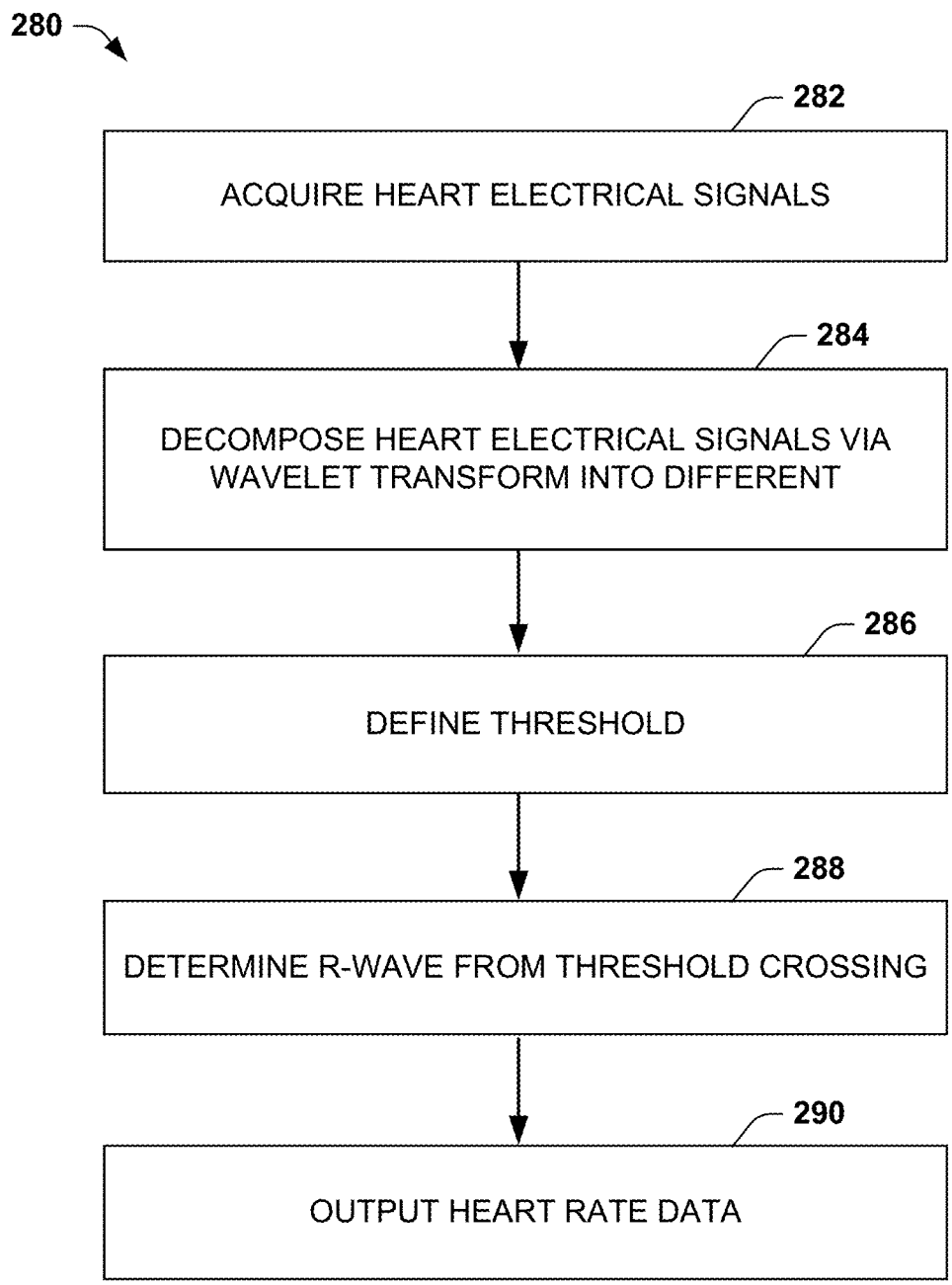
FIG. 18 is a flow diagram illustrating an example of a method to detect part of a heart rate signal.

In view of the foregoing examples, various example embodiments will be better appreciated with reference to methods demonstrated via flow diagrams in FIGS. 17-18. While, for purposes of simplicity of explanation, the example methods of FIGS. 17 and 18 is shown and described as executing serially, the present examples are not limited by the illustrated order, as some actions could in other examples occur in different orders and/or concurrently from that shown and described herein. Moreover, it is not necessary that all described actions be performed to implement a method and other actions can be combined with those shown as disclosed herein. Each of the example methods of FIGS. 17 and 18 can be implemented as computer-readable instructions that can be stored in a non-transitory computer readable medium, such as can be computer program product. The computer readable instructions corresponding to the method of FIG. 17 or 18 can also be executed by a processor.

FIG. 17 is a flow diagram depicting an example of a method 250 that can be utilized for diagnosing a seizure. For instance, the method 250 can discriminate between different types of seizures, such as epileptic and non-epileptic seizures. In the example of FIG. 17, the method can be performed in conjunction with the patient having a seizure, at 252. Timing of the seizure can be identified at 254. At seizure onset, for example, an input can be activated or triggered to designate seizure onset. Similarly, the same or different input can be activated or to designate seizure offset when the seizure ends. In some examples, the input or trigger can be manually provided, such as in response to a user input. Such user input can be provided by the patient or other bystander (e.g., a family member or healthcare provider). In other examples, the input can be provided automatically (e.g., from a sensor or similar device configured to detect the occurrence of a seizure) to designate seizure onset.

At 256, heart electrical data is obtained for a given patient. The heart electrical data can be provided by a cardiac monitoring device (e.g., one or more body surface electrodes). The heart electrical data can be provided as analog data or digital data. At 258, the given patient's heart rate can be determined based on the heart electrical data.

For example, to obtain heart rate information sufficient for diagnosing the seizure, one or more EKG leads is attached to the patient for sensing heart electrical activity of the patient, such as can correspond to an existing type of EKG device or a device (e.g., one or more electrodes) specially adapted for implementing the method of FIG. 17. The heartbeat can be detected from the EKG signal, such as disclosed herein, to provide heartbeat data that can be stored in memory. For example, the heart rate for the patient can be ascertained based on the beat-to-beat (R-R) intervals, such as disclosed herein (see, e.g., FIG. 18 and the corresponding description). The heart rate for the given patient can be stored in memory for further processing.

At 260, the heart rate detected at 258 can be analyzed, such as can include preictal, postictal or both preictal and postictal analysis. As an example, the heart rate data can be processed (e.g., by a processor executing instructions) to calculate one or more indices, such as disclosed herein (e.g., by the index calculator 26 of FIG. 1). Based upon the one or more indices that are computed, the seizure can be classified at 262. For instance, the classification of the seizure can include discriminating the seizure diagnosis as non-epileptic (e.g., PNES) or epileptic. The classification can be utilized to generate an output that can include one or more of: data that is stored in memory, a report (printed or sent to a display), a value or score indicating the likelihood of a given type of seizure. In some examples, the output seizure likelihood can be provided based upon the evaluation and analysis of the one or more indices that has been computed.

FIG. 18 is a flow diagram demonstrating an example of a method 280 that can be utilized for detecting an R-wave, which can be employed for accurately determining an R-R interval. In the example of FIG. 18, raw heart electrical data is acquired at 282. The raw data can be provided as real time EKG data (e.g., at an output of an EKG device) or be stored as computer readable data in corresponding memory.

At 284, the heart electrical signals are decomposed via wavelet transform into different components. For instance, complex wavelet decomposition of the raw data can be performed to localize waveform features of the EKG signals in both time and scale. For example, the complex wavelet decomposition can be performed via a double-tree (also known as dual-tree) wavelet transform, although other types of complex time-invariant wavelet transforms can be utilized. The wavelet decomposition thus exposes features of the decomposed signals in both frequency and time.

At 286, a corresponding threshold is defined. For example, an adaptive threshold can be defined to localize in time and extract the R-waves from the decomposed signals. At 288, the threshold can be applied to the decomposed wavelet signal to detect an R-wave based upon the decomposed signal crossing the threshold. The threshold can be adaptive and set based upon the analysis of the peak and standard deviation of the decomposed signal features.

Each R-wave detected can provide a corresponding index that can be converted via an inverse transform into a time that corresponds to the peak of the R-wave. At 290, the heart rate (e.g., the R-R interval) can be computed. For example, detected R-waves can be employed to compute the R-R interval for consecutive beats, such as based on a difference between time indices computed for one or more consecutive pair of detected R-waves.

The time or index can further be provided to an output for display. In one example, the computed R-wave times (e.g., corresponding to the peak of the R-waves) can be superimposed onto a corresponding display of the EKG signals for a given patient as confirmation of their accuracy. The computed R-waves can be utilized in a variety of purposes including but not limited to the seizure diagnosis and classification systems and methods disclosed herein.

In view of the foregoing structural and functional description, those skilled in the art will appreciate that portions of the invention may be embodied as a method, data processing system, or computer program product. Accordingly, these portions of the present invention may take the form of an entirely hardware embodiment, an entirely software embodiment, or an embodiment combining software and hardware, such as shown and described with respect to the computer system of FIG. 19. Furthermore, portions of the invention may be a computer program product on a computer-usable storage medium having computer readable program code on the medium. Any suitable computer-readable medium may be utilized including, but not limited to, static and dynamic storage devices, hard disks, optical storage devices, and magnetic storage devices.

Certain embodiments of the invention have also been described herein with reference to block illustrations of methods, systems, and computer program products. It will be understood that blocks of the illustrations, and combinations of blocks in the illustrations, can be implemented by computer-executable instructions. These computer-executable instructions may be provided to one or more processors of a general purpose computer, special purpose computer, or other programmable data processing apparatus (or a combination of devices and circuits) to produce a machine, such that the instructions, which execute via the processor, implement the functions specified in the block or blocks.

These computer-executable instructions may also be stored in computer-readable memory that can direct a computer or other programmable data processing apparatus to function in a particular manner, such that the instructions stored in the computer-readable memory result in an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

Figure 19:
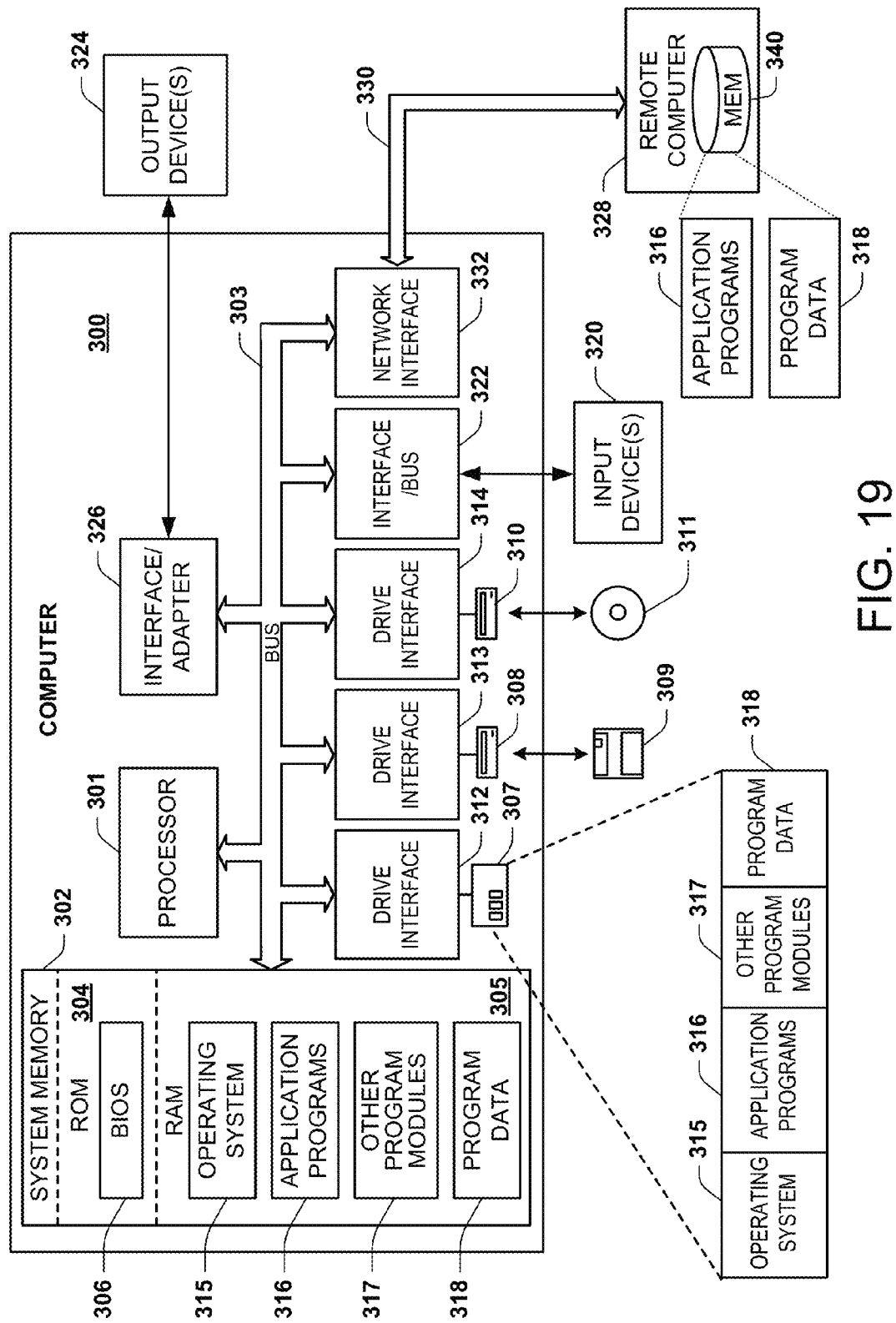
FIG. 19 depicts an example computing environment that can be used to perform methods according to an embodiment of the invention.

In this regard, FIG. 19 illustrates one example of a computer system 300 that can be employed to execute one or more embodiments of the invention, such as including acquisition and processing of sensor data, processing of image data, as well as analysis of transformed sensor data and image data associated with the analysis of cardiac electrical activity. Computer system 300 can be implemented on one or more general purpose networked computer systems, embedded computer systems, routers, switches, server devices, client devices, various intermediate devices/nodes, stand alone computer systems or cloud computing architecture. Additionally, computer system 300 can be implemented on various mobile clients such as, for example, a personal digital assistant (PDA), smart phone, tablet computer, laptop computer, pager, and the like, provided it includes sufficient processing capabilities.

Computer system 300 includes processing unit 301, system memory 302, and system bus 303 that couples various system components, including the system memory, to processing unit 301. Dual microprocessors and other multi-processor architectures also can be used as processing unit 301. System bus 303 may be any of several types of bus structure including a memory bus or memory controller, a peripheral bus, and a local bus using any of a variety of bus architectures. System memory 302 includes read only memory (ROM) 304 and random access memory (RAM) 305. A basic input/output system (BIOS) 306 can reside in ROM 304 containing the basic routines that help to transfer information among elements within computer system 300.

Computer system 300 can include a hard disk drive 307, magnetic disk drive 308, e.g., to read from or write to removable disk 309, and an optical disk drive 310, e.g., for reading CD-ROM disk 311 or to read from or write to other optical media. Hard disk drive 307, magnetic disk drive 308, and optical disk drive 310 are connected to system bus 303 by a hard disk drive interface 312, a magnetic disk drive interface 313, and an optical drive interface 314, respectively. The drives and their associated computer-readable media provide nonvolatile storage of data, data structures, and computer-executable instructions for computer system 300. Although the description of computer-readable media above refers to a hard disk, a removable magnetic disk and a CD, other types of media that are readable by a computer, such as magnetic cassettes, flash memory cards, digital video disks and the like, in a variety of forms, may also be used in the operating environment; further, any such media may contain computer-executable instructions for implementing one or more parts of the algorithms or methods disclosed herein.

A number of program modules may be stored in drives and RAM 305, including operating system 315, one or more application programs 316, other program modules 317, and program data 318. The application programs and program data can include functions and methods programmed to acquire, process and display electrical data from one or more sensors, such as shown and described herein. The application programs and program data can include functions and methods programmed to perform the functionality disclosed herein. For instance, the application programs and data can be programmed to compute and classify a seizure as epileptic or non-epileptic, such as disclosed in relation to FIGS. 1-4. Additionally or alternatively, the application programs and data can be programmed to detect R-waves and compute R-R intervals for defining a patient's heart rate such as disclosed in relation to FIG. 18.

A user may enter commands and information into computer system 300 through one or more input devices 320, such as a pointing device (e.g., a mouse, touch screen), keyboard, microphone, joystick, game pad, scanner, and the like. For instance, the user can employ input device 320 to edit or modify a domain model. These and other input devices 320 are often connected to processing unit 301 through a corresponding port interface 322 that is coupled to the system bus, but may be connected by other interfaces, such as a parallel port, serial port, or universal serial bus (USB). One or more output devices 324 (e.g., display, a monitor, printer, projector, or other type of displaying device) is also connected to system bus 303 via interface 326, such as a video adapter.

Computer system 300 may operate in a networked environment using logical connections to one or more remote computers, such as remote computer 328. Remote computer 328 may be a workstation, computer system, router, peer device, or other common network node, and typically includes many or all the elements described relative to computer system 300. The logical connections, schematically indicated at 330, can include a local area network (LAN) and a wide area network (WAN).

When used in a LAN networking environment, computer system 300 can be connected to the local network through a network interface or adapter 332. When used in a WAN networking environment, computer system 300 can include a modem, or can be connected to a communications server on the LAN. The modem, which may be internal or external, can be connected to system bus 303 via an appropriate port interface. In a networked environment, application programs 316 or program data 318 depicted relative to computer system 300, or portions thereof, may be stored in a remote memory storage device 340.

What have been described above are examples. It is, of course, not possible to describe every conceivable combination of components or methodologies, but one of ordinary skill in the art will recognize that many further combinations and permutations are possible. Accordingly, the invention is intended to embrace all such alterations, modifications, and variations that fall within the scope of this application, including the appended claims. As used herein, the term "includes" means includes but not limited to, the term "including" means including but not limited to. The term "based on" means based at least in part on. Additionally, where the disclosure or claims recite "a," "an," "a first," or "another" element, or the equivalent thereof, it should be interpreted to include one or more than one such element, neither requiring nor excluding two or more such elements.

What is claimed is:

1. A non-transitory machine readable medium having instructions to perform a method comprising:
   detecting a preictal heart rate associated with a given event for a patient, the preictal heart rate being a heart rate detected during a time period prior to a beginning of the given event;
   detecting a postictal heart rate associated with the given event, the postictal heart rate being a heart rate detected during a time period after the given event;
   calculating at least one heart rate index based on a comparative analysis of the postictal heart rate relative to the preictal heart rate;
   determining whether the given event is an epileptic seizure event or a non-epileptic event based on the heart rate index; and
   providing an output identifying the given event as being epileptic or non-epileptic based on the determination of the given event.

2. The medium of claim 1, wherein the heart rate index is calculated to determine a relative heart rate change between the preictal heart rate and the postictal heart rate.

3. The medium of claim 1, wherein the method further comprises comparing the heart rate index relative to a threshold to classify the given event.

4. The medium of claim 1, wherein calculating the heart rate index further comprises:
   determining at least one of a short-term or long-term heart rate variability for a preictal period associated with the given event;
   determining at least one of a short-term or long-term heart rate variability for the postictal period associated with the given event; and
   comparing the short-term or long-term heart rate variability for the preictal period relative to the postictal period, the given event being classified as an epileptic seizure event or as a non-epileptic event based on the comparing.

5. The medium of claim 4, wherein the comparing further comprises computing a ratio of the preictal short-term or long-term variability relative to the postictal short-term or long-term variability.

6. The medium of claim 1, wherein calculating the heart rate index further comprises:
   determining a preictal ratio of short-term heart rate variability and long-term heart rate variability for a preictal period associated with the given event;
   determining a postictal ratio of short-term heart rate variability and long-term heart rate variability for the postictal period associated with the given event; and
   comparing the preictal ratio relative to the postictal ratio, the given event being classified as an epileptic seizure event or as a non-epileptic event based on the comparison.

7. The medium of claim 6, wherein the comparing further comprises computing a ratio of the preictal ratio relative to the postictal ratio.

8. The medium of claim 1, wherein calculating the heart rate index further comprises:
   determining at least one of a low frequency or high frequency index for characterizing a preictal period associated with the given event;
   determining at least one of a low frequency or high frequency index for characterizing a postictal period associated with the given event; and
   comparing the low frequency or high frequency index for the preictal period relative to the low frequency or high frequency index for the postictal period,
   the given event being classified as an epileptic seizure event or as a non-epileptic event based on the comparison.

9. The medium of claim 8, wherein the method further comprises:
   determining a preictal time series representation of beat-to-beat heart rate for the preictal period;
   determining a postictal time series representation of beat-to-beat heart rate for the postictal period;
   analyzing each of the preictal time series representation and the postictal time series representation in the frequency domain to provide an indication of high frequency and low frequency heart rate information for each of the preictal and postictal periods;
   computing a frequency index as a function of the high frequency and low frequency heart rate information; and
   the given event being classified as an epileptic seizure event or as a non-epileptic event based on the frequency index.

10. The medium of claim 1, wherein quantifying further comprises:
    computing a first index to classify the given event as epileptic or non-epileptic;
    computing a second index to classify the given event as epileptic or non-epileptic; and
    providing an output to classify the given event as an epileptic seizure event or as a non-epileptic event based on the first index and the second index.

11. The medium of claim 10, wherein the method further comprises:
    determining a first of the at least two indices; and
    determining whether to compute the second index based on the value of the first index.

12. The medium of claim 1, wherein detecting the heart rate for each of the preictal and postictal periods is detected by computing a time invariant complex wavelet of heart electrical signals for each of the preictal and postictal periods.

13. The medium of claim 1, wherein detecting the heart rate for each of the preictal and postictal periods further comprises:
    receiving a time-based signal representing heart electrical activity for the patient during the respective period;
    decomposing the time-based signal via a time-invariant complex wavelet to provide a complex wavelet representation;

thresholding the complex wavelet representation to provide an index corresponding to a time for each R-wave in the decomposed signal; and computing an R-R interval, corresponding to the heart rate, based on the indices for a pair of consecutive R-waves.

14. The medium of claim 1 in which the given event is a motor-type seizure.

15. The medium of claim 2, wherein calculating the heart rate index further comprises:

determining at least one of a short-term or long-term heart rate variability for a preictal period associated with the given event;

determining at least one of a short-term or long-term heart rate variability for the postictal period associated with the given event; and comparing the short-term or long-term heart rate variability for the preictal period relative to the postictal period.

16. The medium of claim 2, wherein calculating the heart rate index further comprises:

determining a preictal ratio of short-term heart rate variability and long-term heart rate variability for a preictal period associated with the given event;

determining a postictal ratio of short-term heart rate variability and long-term heart rate variability for the postictal period associated with the given event; and comparing the preictal ratio relative to the postictal ratio.

17. The medium of claim 4, wherein calculating the heart rate index further comprises determining a relative heart rate change between the preictal heart rate and the postictal heart rate.

18. The medium of claim 6, wherein calculating the heart rate index further comprises determining a relative heart rate change between the preictal heart rate and the postictal heart rate.

19. The medium of claim 2, wherein the heart rate index is computed by dividing the difference between the postictal heart rate and the preictal heart rate by a variability of the preictal heart rate.

20. The medium of claim 19, wherein the variability of the preictal heart rate is computed as a standard deviation of the preictal heart rate.

21. The medium of claim 1, further comprising diagnosing the non-epileptic event as one of a physiological non-epileptic seizure, a psychogenic non-epileptic seizure, or a malingering non-epileptic event.

22. The medium of claim 1, further comprising identifying an occurrence of the given event.

23. The method of claim 22, wherein the identifying is performed in response to a user input designating an occurrence of the given event.

24. The method of claim 22, wherein the identifying is performed automatically based on heart rate measurement data that includes the detected preictal and postictal heart rates.

25. The method of claim 22, wherein the identifying the given event is performed based on an input from a sensor.

26. An apparatus to discriminate between epileptic and non-epileptic events, comprising:

non-transitory memory to store heart electrical measurement data for at least before and after a given event;

a processor to access and execute instructions stored in the memory, the instructions comprising:

an interval selector method programmed to designate the heart electrical measurement data as preictal heart electrical data or postictal heart electrical data, the preictal heart electrical data being detected during a time period prior to a beginning of the given event, and the postictal heart electrical data being detected during a time period after the given event;

an index calculator method programmed to determine an index based on a comparative analysis of the preictal heart electrical data relative to the postictal heart electrical data, the index quantifying a relationship between postictal heart electrical activity and preictal heart electrical activity;

a classifier method programmed to indicate whether the given event is an epileptic seizure event or a non-epileptic event based on the index.

27. The apparatus of claim 26, wherein the index calculator is further programmed to determine the index according to a relative heart rate change between the preictal heart rate and the postictal heart rate.

28. The apparatus of claim 26, wherein the index calculator further comprises:

a preictal index calculator method to determine at least one of a short-term or long-term heart rate variability for a preictal period associated with the given event;

a postictal index calculator method to determine at least one of a short-term or long-term heart rate variability for the postictal period associated with the given event; and the instructions further comprising:

a comparator method to compare the short-term or long-term heart rate variability for the preictal period relative to the postictal period, the given event being classified as an epileptic seizure event or as a non-epileptic event based on the comparison.

29. The apparatus of claim 26, wherein the index calculator further comprises a frequency index calculator to determine at least one of a low frequency or high frequency index for characterizing a preictal period associated with the given event and to determined at least one of a low frequency or high frequency index for characterizing a postictal period associated with the given event; and the instructions further comprising:

a comparator to compare the low frequency or high frequency index for the preictal period relative to the low frequency or high frequency index for the postictal period, the given event being classified as an epileptic seizure event or as a non-epileptic event based on the comparison.

30. The apparatus of claim 29, wherein the instructions further comprise:

a time series converter to determine a preictal time series representation of beat-to-beat heart rate for the preictal period and to determine a postictal time series representation of beat-to-beat heart rate for the postictal period;

frequency domain analysis to analyze each of the preictal time series representation and the postictal time series representation in the frequency domain to provide an indication of high frequency and low frequency heart rate information for each of the preictal and postictal periods;

the frequency calculator computing the frequency index as a function of the high frequency and low frequency heart rate information, the given event being classified as an epileptic seizure event or as a non-epileptic event based on the frequency index.

31. The apparatus of claim 26, wherein the instructions further comprises:

a preictal heart rate calculator and a postictal heart rate calculator, each being programmed to
receive a time-based signal representing heart electrical activity for the patient during the respective period;

decompose the time-based signal via a time-invariant complex wavelet to provide a complex wavelet representation;

threshold the complex wavelet representation to provide an index corresponding to a time for each R-wave in the decomposed signal; and compute an R-R interval, corresponding to the heart rate, based on the indices for a pair of consecutive R-waves.

32. The apparatus of claim 27, wherein the index calculator further comprises:

a preictal index calculator to determine at least one of a short-term or long-term heart rate variability to provide a preictal index for a preictal period associated with the given event;

a postictal index calculator to determine at least one of a short-term or long-term heart rate variability for the postictal period associated with the given event; and the instructions further comprising:

a comparator to compare the short-term or long-term heart rate variability for the preictal period relative to the postictal period, the given event being classified as an epileptic seizure event or as a non-epileptic event based on the comparison.

33. The apparatus of claim 28, wherein the index calculator is further programmed to determine the index according to a relative heart rate change between the preictal heart rate and the postictal heart rate.

34. The apparatus of claim 26, wherein the index calculator is further programmed to compute the index by dividing the difference between the postictal heart rate and the preictal heart rate by a variability of the preictal heart rate.

35. The apparatus of claim 34, wherein the index calculator is further programmed to compute the variability of the preictal heart rate as a standard deviation of the preictal heart rate.

36. A method to discriminate between epileptic and non-epileptic events comprising:

identifying a given event for a patient;

detecting a preictal heart rate associated with the given event for the patient, the preictal heart rate being a heart rate detected during a time prior to a beginning of the given event;

detecting a postictal heart rate associated with the given event, the postictal heart rate being a heart rate detected during a time after the given event;

determining the given event as being one of an epileptic seizure event or a non-epileptic event based on a comparative analysis of the postictal heart rate relative to the preictal heart rate; and providing an output specifying the given event as being epileptic or non-epileptic based on the determination of the given event.

37. The method of claim 36, wherein the identifying of the given event is performed based on at least one of a user input and an input from a sensor.

* * * * *